United States Patent
Stefano et al.

(10) Patent No.: US 10,639,322 B2
(45) Date of Patent: May 5, 2020

(54) METHODS AND MATERIALS FOR REDUCING AMYLOID BETA LEVELS WITHIN A MAMMAL

(71) Applicant: THE RESEARCH FOUNDATION FOR THE STATE UNIVERSITY OF NEW YORK, Albany, NY (US)

(72) Inventors: George B. Stefano, Melville, NY (US); Richard M. Kream, Huntington, NY (US); Kirk J. Mantione, Patchogue, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 15/562,149

(22) PCT Filed: Mar. 25, 2016

(86) PCT No.: PCT/US2016/024295
§ 371 (c)(1),
(2) Date: Sep. 27, 2017

(87) PCT Pub. No.: WO2016/160594
PCT Pub. Date: Oct. 6, 2016

(65) Prior Publication Data
US 2018/0078575 A1    Mar. 22, 2018

Related U.S. Application Data

(60) Provisional application No. 62/139,178, filed on Mar. 27, 2015.

(51) Int. Cl.
| | | |
|---|---|---|
| *A61K 31/718* | (2006.01) | |
| *A61K 36/81* | (2006.01) | |
| *A61K 9/00* | (2006.01) | |
| *A61K 9/08* | (2006.01) | |
| *A61P 25/28* | (2006.01) | |
| *A61K 9/20* | (2006.01) | |
| *A61K 31/355* | (2006.01) | |
| *A61K 31/385* | (2006.01) | |

(52) U.S. Cl.
CPC .......... *A61K 31/718* (2013.01); *A61K 9/0053* (2013.01); *A61K 9/08* (2013.01); *A61K 9/20* (2013.01); *A61K 31/355* (2013.01); *A61K 31/385* (2013.01); *A61K 36/81* (2013.01); *A61P 25/28* (2018.01)

(58) Field of Classification Search
None
See application file for complete search history.

(56) References Cited

U.S. PATENT DOCUMENTS

| | | |
|---|---|---|
| 2,134,714 A | 11/1938 | Glassman |
| 3,622,677 A | 11/1971 | Short |
| 7,041,730 B2 | 5/2006 | Rogers et al. |
| 7,098,239 B2 | 8/2006 | Edmondson et al. |
| 7,590,493 B2 | 9/2009 | Menderick et al. |
| 7,893,252 B2 | 2/2011 | Platt et al. |
| 2003/0159178 A1 | 8/2003 | Ulvskov et al. |
| 2003/0187058 A1 | 10/2003 | Hasselwander et al. |
| 2004/0038933 A1 | 2/2004 | Kaneko et al. |
| 2005/0031651 A1 | 2/2005 | Gervais et al. |
| 2005/0085498 A1 | 4/2005 | Byrd |
| 2005/0180962 A1 | 8/2005 | Raz et al. |
| 2005/0214413 A1 | 9/2005 | McAnalley et al. |
| 2006/0264383 A1 | 11/2006 | Kingston |
| 2008/0213400 A1 | 9/2008 | Fine et al. |
| 2008/0279984 A1 | 11/2008 | Kalum et al. |
| 2010/0129333 A1 | 5/2010 | Kawakami et al. |
| 2010/0143513 A1* | 6/2010 | Lee ................... A61K 31/715 424/750 |
| 2011/0077217 A1 | 3/2011 | Platt et al. |
| 2011/0081475 A1 | 4/2011 | Huber et al. |
| 2013/0259870 A1 | 10/2013 | Traber et al. |
| 2013/0309355 A1 | 11/2013 | Wong et al. |
| 2013/0315826 A1 | 11/2013 | Mukherjee et al. |
| 2014/0024602 A1 | 1/2014 | Sundaram et al. |
| 2015/0065451 A1 | 3/2015 | Stefano |
| 2016/0243152 A1 | 8/2016 | Stefano et al. |

(Continued)

FOREIGN PATENT DOCUMENTS

| | | |
|---|---|---|
| CN | 103110657 | 5/2013 |
| JP | 2001-511153 | 8/2001 |

(Continued)

OTHER PUBLICATIONS

Alikhani, J Bioenerg Biomembr (2009) 41:447-451.*
Nelson, Nutritional Neuroscience 2012, vol. 15, No. 4, pp. 149-162.*
Benz et al., "Tonal nitric oxide and health—a free radical and a scavenger of free radicals," *Med Sci Monit.*, 8(1):RA1-4, Jan. 2002.
Brand and Wheeler, "KRAS mutant colorectal tumors: past and present," *Small GTPases.*, 3(1):34-39, Jan.-Mar. 2012.
Carley and Severson, "Fatty acid metabolism is enhanced in type 2 diabetic hearts," *Biochim Biophys Acta.*, 1734(2):112-126, Epub Apr. 9, 2005.

(Continued)

*Primary Examiner* — Layla D Berry
(74) *Attorney, Agent, or Firm* — Fish & Richardson P.C.

(57) ABSTRACT

This document provides methods and materials for reducing amyloid beta levels within a mammal (e.g. a mammal having Alzheimer's disease). For example, this document provides methods for using compositions containing a potato polysaccharide preparation to reduce one or more symptoms of Alzheimer's disease. In some cases, a composition containing a potato polysaccharide preparation provided herein can be used to increase binding, sequestration, and/or degradation of CNS-derived amyloid beta polypeptides, thereby inhibiting the formation of neurofibrillary plaques.

16 Claims, 37 Drawing Sheets

(56) References Cited

U.S. PATENT DOCUMENTS

| | | | |
|---|---|---|---|
| 2017/0232033 A1 | 8/2017 | Stefano et al. | |
| 2018/0078599 A1 | 3/2018 | Stefano et al. | |

FOREIGN PATENT DOCUMENTS

| | | | |
|---|---|---|---|
| JP | 2004-508399 | 3/2004 | |
| JP | 2006-321784 | 11/2006 | |
| JP | 2007-024871 | 2/2007 | |
| JP | 2007-509178 | 4/2007 | |
| JP | 2009-007309 | 1/2009 | |
| JP | 2012-149004 | 8/2012 | |
| KR | 101093413 | 12/2011 | |
| WO | WO 1998/033494 | 8/1998 | |
| WO | WO 2002/22111 | 3/2002 | |
| WO | WO 2005/039539 | 5/2005 | |
| WO | WO 2006/114019 | 11/2006 | |
| WO | WO 2011/069781 | 6/2011 | |
| WO | WO 2012/016050 | 2/2012 | |
| WO | WO 2013/040316 | 3/2013 | |
| WO | WO 2013/148282 | 10/2013 | |
| WO | WO-2013148282 A1 * | 10/2013 | ........... A61K 31/355 |
| WO | WO 2015/041837 | 3/2015 | |
| WO | WO 2017/160678 | 9/2017 | |

OTHER PUBLICATIONS

Chetty and Govender, "Gene of the month: KRAS," *J Clin Pathol.*, 66(7):548-550, Epub Apr. 27, 2013.

Congiu et al., "Expression of common housekeeping genes is affected by disease in human hepatitis C virus-infected liver," *Liver Int.*, 31(3):386-390, Epub Nov. 15, 2010.

Constantin-Teodosiu et al., "The role of FOXO and PPAR transcription factors in diet-mediated inhibition of PDC activation and carbohydrate oxidation during exercise in humans and the role of pharmacological activation of PDC in overriding these changes," *Diabetes*, 61(5):1017-1024, Epub Feb. 7, 2012.

Cooper et al., "Molecular biology of lung cancer," *J Thorac Dis.*, 5 Suppl 5:S479-S490, Oct. 2013.

De la Torre and Stefano, "Evidence that Alzheimer's disease is a microvascular disorder: the role of constitutive nitric oxide," *Brain Res Brain Res Rev.*, 34(3):119-136, Dec. 2000.

De la Torre, "Alzheimer's disease is a vasocognopathy: a new term to describe its nature," *Neurol Res.*, 26(5):517-524, Jul. 2004.

De la Torre, "Is Alzheimer's disease a neurodegenerative or a vascular disorder? Data, dogma, and dialectics," *Lancet Neurol.*, 3(3):184-190, Mar. 2004.

Deane et al., "Clearance of amyloid-beta peptide across the blood-brain barrier: implication for therapies in Alzheimer's disease," *CNS Neurol Disord Drug Targets*, 8(1):16-30, Mar. 2009.

Di Magliano and Logsdon, "Roles for KRAS in pancreatic tumor development and progression," *Gastroenterology*, 144(6):1220-1229, Jun. 2013.

Ekstrand et al., "Mitochondrial transcription factor A regulates mtDNA copy number in mammals," *Hum Mol Genet.*, 13(9):935-944. Epub Mar. 11, 2004.

Franks et al., "Viral p21 Ki-RAS protein: a potent intracellular mitogen that stimulates adenylate cyclase activity in early G1 phase of cultured rat cells," *J Cell Biochem.*, 33(2):87-94, Feb. 1987.

Freude et al., "Neuronal IGF-1 resistance reduces Abeta accumulation and protects against premature death in a model of Alzheimer's disease," *Faseb J.*, 23(10):3315-3324, Epub Jun. 1, 2009.

Friedman, "Analysis of biologically active compounds in potatoes (Solanum tuberosum), tomatoes (Lycopersicon esculentum), and jimson weed (Datura stramonium) seeds," *J Chromatogr A.*, 1054(1-2):143-155, Oct. 29, 2004.

Friedman, "Potato glycoalkaloids and metabolites: roles in the plant and in the diet," *J Agric Food Chem.*, 54(23):8655-8681, Nov. 15, 2006.

Fry, "The Structure and Functions of Xyloglucan," Journal of Experimental Botany, 1989, 40(210):1-11.

Galperin et al., "Shoc2 is targeted to late endosomes and required for Erk1/2 activation in EGF-stimulated cells," *PLoS One*, 7(5):e36469, Epub May 14, 2012.

Gao et al., "Effect of solanine on the membrane potential of mitochondria in HepG2 cells and [Ca2+]i in the cells," *World J Gastroenterol.*, 12(21):3359-3367, Jun. 7, 2006.

GenBank® Accession No. AAA52712.1 (GI No. 184556) "insulin-degrading enzyme [*Homo sapiens*]" Nov. 8, 1994, 2 pages.

GenBank® Accession No. AAD13528.1 (GI No. 4240387) "PTEN [*Homo sapiens*]" 1 page, Feb. 8, 1999.

GenBank® Accession No. AAD24775.1 (GI No. 4581877) "proline dehydrogenase [*Homo sapiens*]" 1 page, Apr. 13, 1999.

GenBank® Accession No. AAH00408.1 (GI No. 12653279) "ACAT2 protein [*Homo sapiens*]" 2 pages, Jun. 9, 2008.

GenBank® Accession No. AAH00484.1 (GI No. 12653427) "UQCRC2 protein [*Homo sapiens*]" 2 pages, Aug. 3, 2004.

GenBank® Accession No. AAH00583.2 (GI No. 38014202) "THOP1 protein, partial [*Homo sapiens*]" 2 pages, Nov. 4, 2003.

GenBank® Accession No. AAH04243.2 (GI No. 48257075) "BCAT2 protein, partial [*Homo sapiens*]" 2 pages, Jun. 4, 2004.

GenBank® Accession No. AAH04905.2 (GI No. 33872889) "MRPS2 protein [*Homo sapiens*]" 2 pages, Sep. 16, 2003.

GenBank® Accession No. AAH08028.2 (GI No. 34782901) "ATP5A1 protein, partial [*Homo sapiens*]" 2 pages, Jan. 19, 2006.

GenBank® Accession No. AAH10704.1 (GI No. 14715079) "SH2B1 protein [*Homo sapiens*]" 2 pages, Jul. 24, 2006.

GenBank® Accession No. AAH13410.1 (GI No. 38196950) "AGPAT4 protein, partial [*Homo sapiens*]" 2 pages, Jul. 28, 2005.

GenBank® Accession No. AAH16934.1 (GI No. 16877367) "SOD2 protein [*Homo sapiens*]" 2 pages, Oct. 7, 2003.

GenBank® Accession No. AAH20695.1 (GI No. 116283350) "CPS1 protein, partial [*Homo sapiens*]" 2 pages, Sep. 11, 2007.

GenBank® Accession No. AAH22071.1 (GI No. 34784795) "Glutathione peroxidase 4 (phospholipid hydroperoxidase) [*Homo sapiens*]" Jul. 17, 2006, 2 pages.

GenBank® Accession No. AAH31485.1 (GI No. 32425437) "ACACA protein, partial [*Homo sapiens*]" 2 pages, Jan. 6, 2005.

GenBank® Accession No. AAH33692.1 (GI No. 21707182) "HMGCR protein [*Homo sapiens*]" 2 pages, Sep. 1, 2006.

GenBank® Accession No. AAH40239.1 (GI No. 25955471) "PDK4 protein [*Homo sapiens*]" 2 pages, Jun. 19, 2006.

GenBank® Accession No. AAH41143.1 (GI No. 26996542) "ACBD4 protein [*Homo sapiens*]" 2 pages, Nov. 19, 2003.

GenBank® Accession No. AAH47528.1 (GI No. 28839408) "TOMM40 protein [*Homo sapiens*]" 2 pages, Jul. 28, 2005.

GenBank® Accession No. AAH47784.1 (GI No. 29126836) "MRPS9 protein, partial [*Homo sapiens*]" 2 pages, Sep. 16, 2003.

GenBank® Accession No. AAH68050.1 (GI No. 45751586) "CASP8 protein [*Homo sapiens*]" 2 pages, Sep. 9, 2005.

GenBank® Accession No. AAH70041.1 (GI No. 47124456) "Lipase, hormone-sensitive [*Homo sapiens*]" 2 pages, Jul. 17, 2006.

GenBank® Accession No. AAH94760.1 (GI No. 66267554) "PDHA2 protein, partial [*Homo sapiens*]" 2 pages, May 27, 2005.

GenBank® Accession No. AAI30284.1 (GI No. 120660146) "Nitric oxide synthase 2, inducible [*Homo sapiens*]" Mar. 18, 2009, 3 pages.

GenBank® Accession No. AAI44252.1 (GI No. 219518198) "PPARGC1B protein [*Homo sapiens*]" 2 pages, Mar. 18, 2009.

GenBank® Accession No. ABD77240.1 (GI No. 89574029) "mitochondrial ATP synthase, H+ transporting F1 complex beta subunit, partial [*Homo sapiens*]" 1 page, Jul. 18, 2006.

GenBank® Accession No. ABQ58815.1 (GI No. 148300624) "PDHA1, partial [*Homo sapiens*]" 1 page, May 30, 2007.

GenBank® Accession No. ACN89883.1 (GI No. 225421341) "mitochondrial aldehyde dehydrogenase 4 family member A1 transcript variant ALDH4A1_v6 [*Homo sapiens*]" 1 page, Jan. 1, 2010.

GenBank® Accession No. AFL91689.1 (GI No. 390432195) "fatty acid desaturase 1, partial [*Homo sapiens*]" 1 page, Aug. 28, 2012.

GenBank® Accession No. AK314199.1 (GI No. 164697148) "*Homo sapiens* cDNA, FLJ94925, *Homo sapiens* fatty acid desaturase 1 (FADS1), mRNA" 2 pages, May 24, 2008.

GenBank® Accession No. BAD13700.1 (GI No. 46091143) "MRPS18B protein [*Homo sapiens*]" 1 page, Sep. 13, 2006.

(56) References Cited

OTHER PUBLICATIONS

GenBank® Accession No. CAB94757.1 (GI No. 8574070) "NFKB1 [*Homo sapiens*]" 2 pages, Nov. 14, 2006.
GenBank® Accession No. CAG28581.1 (GI No. 47115243) "TFAM, partial [*Homo sapiens*]" 2 pages, Oct. 16, 2008.
GenBank® Accession No. CAG28601.1 (GI No. 47115283) "ILK, partial [*Homo sapiens*]," May 10, 2014, 2 pages.
GenBank® Accession No. CAG32985.1 (GI No. 48145525) "NR4A1 [*Homo sapiens*]" 2 pages, Oct. 16, 2008.
GenBank® Accession No. CAG33001.1 (GI No. 48145557) "MRPL3 [*Homo sapiens*]"2 pages, Oct. 16, 2008.
GenBank® Accession No. CAG33165.1 (GI No. 48145885) "HMGCL [*Homo sapiens*]" 2 pages, Oct. 16, 2008.
GenBank® Accession No. CAG33194.1 (GI No. 48145943) "PCK2 [*Homo sapiens*]" 2 pages, Oct. 16, 2008.
GenBank® Accession No. CAG33335.1 (GI No. 4814622) "LPL [*Homo sapiens*]" 2 pages, Oct. 16, 2008.
GenBank® Accession No. CAG33384.1 (GI No. 48146323) "LYPLA1 [*Homo sapiens*]" 2 pages, Oct. 16, 2008.
GenBank® Accession No. CAG33458.1 (GI No. 48146471) "MRPL17 [*Homo sapiens*]" 2 pages, Oct. 16, 2008.
GenBank® Accession No. CAG38562.1 (GI No. 49065488) "MRPL15 [*Homo sapiens*]" 2 pages, Oct. 16, 2008.
GenBank® Accession No. CAG38785.1 (GI No. 49168580) "MDH2 [*Homo sapiens*]" 2 pages, Oct. 16, 2008.
GenBank® Accession No. CR457103.1 (GI No. 48146322) "*Homo sapiens* full open reading frame cDNA clone RZPDo834G067D for gene LYPLA1, lysophospholipase I; complete cds, incl. stopcodon" 2 pages, Oct. 16, 2008.
GenBank® Accession No. CR536548.1 (GI No. 49168579) "*Homo sapiens* full open reading frame cDNA clone RZPDo834E0920D for gene MDH2, malate dehydrogenase 2, NAD (mitochondrial); complete cds, incl. stopcodon" 2 pages, Oct. 16, 2008.
GenBank® Accession No. FJ462711.1 (GI No. 225421340) "*Homo sapiens* mitochondrial aldehyde dehydrogenase 4 family member A1 transcript variant ALDH4A1_v6 (ALDH4A1) mRNA, complete cds; nuclear gene for mitochondrial product," 2 pages, Jan. 1, 2010.
GenBank® Accession No. NC_000005.10 (GI No. 568815593) "*Homo sapiens* chromosome 5, GRCh38 Primary Assembly" Feb. 3, 2014, 2 pages.
GenBank® Accession No. NC_000012.12 (GI No. 568815586) "*Homo sapiens* chromosome 12, GRCh38 Primary Assembly," Feb. 3, 2014, 3 pages.
GenBank® Accession No. NC_000019.10 (GI No. 568815579) "*Homo sapiens* chromosome 19, GRCh38 Primary Assembly," Feb. 3, 2014, 2 pages.
GenBank® Accession No. NG_011470.1 (GI No. 22480926) "*Homo sapiens* nitric oxide synthase 2, inducible (NOS2), RefSeqGene on chromosome 17," Mar. 24, 2014, 15 pages.
GenBank® Accession No. NG_013012.1 (GI No. 260593646) "*Homo sapiens* insulin-degrading enzyme (IDE), RefSeqGene on chromosome 10," Mar. 13, 2014, 32 pages.
GenBank® Accession No. NG_016444 (GI No. 284813599) "*Homo sapiens* low density lipoprotein receptor-related protein 1 (LRP1), RefSeqGene on chromosome 12" Feb. 23, 2014, 32 pages.
GenBank® Accession No. NG_029469 (GI No. 340523104) "*Homo sapiens* heat shock 70kDa protein 9 (mortalin) (HSPA9), RefSeqGene on chromosome 5," Feb. 18, 2014, 10 pages.
GenBank® Accession No. NG_029615.1 (GI No. 342349296) "*Homo sapiens* amyloid beta (A4) precursor protein-binding, family B, member 1 (Fe65) (APBB1), RefSeqGene on chromosome 11," Feb. 18, 2014, 11 pages.
GenBank® Accession No. NM_000098.2 (GI No. 169790951) "*Homo sapiens* carnitine palmitoyltransferase 2 (CPT2), mRNA" 4 pages., May 3, 2014.
GenBank® Accession No. NM_000191.2 (GI No. 62198231) "*Homo sapiens* 3-hydroxymethyl-3-methylglutaryl-CoA lyase (HMGCL), transcript variant 1, mRNA" 4 pages, May 10, 2014.
GenBank® Accession No. NM_000237.1 (GI No. 145275217) "*Homo sapiens* lipoprotein lipase (LPL), mRNA" 4 pages, Apr. 1, 2007.
GenBank® Accession No. NM_000314.2 (GI No. 110224474) "*Homo sapiens* phosphatase and tensin homolog (mutated in multiple advanced cancers 1) (PTEN), mRNA" 24 pages, Aug. 8, 2005.
GenBank® Accession No. NM_000636.1 (GI No. 67782304) "*Homo sapiens* superoxide dismutase 2, mitochondrial (SOD2), mRNA" 10 pages, May 16, 2005.
GenBank® Accession No. NM_000859.2 (GI No. 196049378) "*Homo sapiens* 3-hydroxy-3-methylglutaryl-CoA reductase (HMGCR), transcript variant 1, mRNA" 7 pages, May 25, 2014.
GenBank® Accession No. NM_001001937.1 (GI No. 50345983) "*Homo sapiens* ATP synthase, H+ transporting, mitochondrial F1 complex, alpha subunit 1, cardiac muscle (ATP5A1), nuclear gene encoding mitochondrial protein, transcript variant 1, mRNA" 6 pages, Mar. 11, 2011.
GenBank® Accession No. NM_001014794.2 (GI No. 510785737) "*Homo sapiens* integrin-linked kinase (ILK), transcript variant 2, mRNA," 5 pages.
GenBank® Accession No. NM_001122633.2 (GI No. 327532712) "*Homo sapiens* carbamoyl-phosphate synthase 1, mitochondrial (CPS1), nuclear gene encoding mitochondrial protein, transcript variant 1, mRNA" 7 pages, Mar. 20, 2011.
GenBank® Accession No. NM_001126121.1 (GI No. 186928857) "*Homo sapiens* solute carrier family 25 (mitochondrial thiamine pyrophosphate carrier), member 19 (SLC25A19), nuclear gene encoding mitochondrial protein, transcript variant 1, mRNA" 5 pages, Mar. 11, 2011.
GenBank® Accession No. NM_001128916.1 (GI No. 193083119) "*Homo sapiens* translocase of outer mitochondrial membrane 40 homolog (yeast) (TOMM40), nuclear gene encoding mitochondrial protein, transcript variant 2, mRNA" 4 pages, Mar. 11, 2011.
GenBank® Accession No. NM_001130996.1 (GI No. 196049379) "*Homo sapiens* 3-hydroxy-3-methylglutaryl-CoA reductase (HMGCR), transcript variant 2, mRNA" 6 pages, Mar. 20, 2011.
GenBank® Accession No. NM_001135704.1 (GI No. 209364588) "*Homo sapiens* acyl-CoA binding domain containing 4 (ACBD4), transcript variant 1, mRNA" 4 pages, May 15, 2011.
GenBank® Accession No. NM_001145797.1 (GI No. 224926829) "*Homo sapiens* SH2B adaptor protein 1 (SH2B1), transcript variant 5, mRNA" 7 pages, Mar. 12, 2011.
GenBank® Accession No. NM_001165412.1 (GI No. 25955301) "*Homo sapiens* nuclear factor of kappa light polypeptide gene enhancer in B-cells 1 (NFKB1), transcript variant 2, mRNA" 7 pages, May 22, 2011.
GenBank® Accession No. NM_001173454.1 (GI No. 291084741) "*Homo sapiens* pyruvate dehydrogenase (lipoamide) alpha 1 (PDHA1), nuclear gene encoding mitochondrial protein, transcript variant 2, mRNA" Mar. 11, 2011, 5 pages.
GenBank® Accession No. NM_001190.1 (GI No. 258614013) "*Homo sapiens* branched chain aminotransferase 2, mitochondrial (BCAT2), mRNA" 3 pages, Dec. 23, 2003.
GenBank® Accession No. NM_001191060.1 (GI No. 300796969) "*Homo sapiens* solute carrier family 25 (mitochondrial carrier: glutamate), member 22 (SLC25A22), nuclear gene encoding mitochondrial protein, transcript variant 1, mRNA" 4 pages, Mar. 11, 2011.
GenBank® Accession No. NM_001228.4 (GI No. 122056470) "*Homo sapiens* caspase 8, apoptosis-related cysteine peptidase (CASP8), transcript variant a, mRNA" 5 pages, Mar. 19, 2011.
GenBank® Accession No. NM_001269039.1 (GI No. 392841223) "*Homo sapiens* soc-2 suppressor of clear homolog (C. elegans) (SHOC2), transcript variant 2, mRNA," Mar. 16, 2014, 5 pages.
GenBank® Accession No. NM_001686.3 (GI No. 50345985) "*Homo sapiens* ATP synthase, H+ transporting, mitochondrial F1 complex, beta polypeptide (ATP5B), mRNA" 4 pages, Feb. 27, 2011.
GenBank® Accession No. NM_002015.3 (GI No. 133930787) "*Homo sapiens* forkhead box O1 (FOXO1), mRNA" 5 pages, Mar. 13, 2011.
GenBank® Accession No. NM_002543.2 (GI No. 119392084) "*Homo sapiens* oxidised low density lipoprotein (lectin-like) receptor 1 (OLR1), mRNA" 4 pages, Nov. 17, 2006.

(56) References Cited

OTHER PUBLICATIONS

GenBank® Accession No. NM_002611.4 (GI No. 315630394) "*Homo sapiens* pyruvate dehydrogenase kinase, isozyme 2 (PDK2), nuclear gene encoding mitochondrial protein, transcript variant 1, mRNA" 4 pages, Mar. 11, 2011.
GenBank® Accession No. NM_002612.2 (GI No. 94421466) "*Homo sapiens* pyruvate dehydrogenase kinase, isozyme 4 (PDK4), mRNA" 4 pages, Apr. 16, 2011.
GenBank® Accession No. NM_003201.1 (GI No. 4507400) "*Homo sapiens* transcription factor A, mitochondrial (TFAM), nuclear gene encoding mitochondrial protein, mRNA" 4 pages, Mar. 11, 2011.
GenBank® Accession No. NM_003249.3 (GI No. 34222291) "*Homo sapiens* thimet oligopeptidase 1 (THOP1), mRNA" 4 pages, Mar. 13, 2011.
GenBank® Accession No. NM_003366.2 (GI No. 50592987) "*Homo sapiens* ubiquinol-cytochrome c reductase core protein II (UQCRC2), nuclear gene encoding mitochondrial protein, mRNA" 4 pages, Mar. 10, 2011.
GenBank® Accession No. NM_004563.1 (GI No. 66346720) "*Homo sapiens* phosphoenolpyruvate carboxykinase 2 (mitochondrial) (PCK2), mRNA" 3 pages, Apr. 22, 2005.
GenBank® Accession No. NM_004976.2 (GI No. 15718761) "GTPase KRas isoform b [*Homo sapiens*]," Mar. 16, 2014, 3 pages.
GenBank® Accession No. NM_004985.3 (GI No. 34485723) "*Homo sapiens* Kirsten rat sarcoma viral oncogene homolog (KRAS), transcript variant b, mRNA," Jan. 19, 2014, 6 pages.
GenBank® Accession No. NM_005357.2 (GI No. 21328445) "*Homo sapiens* lipase, hormone-sensitive (LIPE), mRNA" 5 pages, Mar. 12, 2011.
GenBank® Accession No. NM_005390.4 (GI No. 134031963) "*Homo sapiens* pyruvate dehydrogenase (lipoamide) alpha 2 (PDHA2), mRNA" 3 pages, Mar. 12, 2011.
GenBank® Accession No. NM_005891.1 (GI No. 148539871) "*Homo sapiens* acetyl-Coenzyme A acetyltransferase 2 (acetoacetyl Coenzyme A thiolase) (ACAT2), mRNA" 3 pages, Apr. 15, 2007.
GenBank® Accession No. NM_005984.3 (GI No. 374713106) "*Homo sapiens* solute carrier family 25 (mitochondrial carrier; citrate transporter), member 1 (SLC25A1), nuclear gene encoding mitochondrial protein, transcript variant 1, mRNA" 5 pages, Mar. 13, 2011.
GenBank® Accession No. NM_006411.3 (GI No. 301336168) "*Homo sapiens* 1-acylglycerol-3-phosphate O-acyltransferase 1 (lysophosphatidic acid acyltransferase, alpha) (AGPAT1), transcript variant 1, mRNA" 5 pages, Mar. 13, 2011.
GenBank® Accession No. NM_006567.3 (GI No. 126513133) "*Homo sapiens* phenylalanyl-tRNA synthetase 2, mitochondrial (FARS2), nuclear gene encoding mitochondrial protein, mRNA" 5 pages, Mar. 10, 2011.
GenBank® Accession No. NM_007189.2 (GI No. 525345247) "*Homo sapiens* ATP-binding cassette, sub-family F (GCN20), member 2 (ABCF2), nuclear gene encoding mitochondrial protein, transcript variant 1, mRNA" 5 pages, Mar. 12, 2011.
GenBank® Accession No. NM_013261.2 (GI No. 116284374) "*Homo sapiens* peroxisome proliferative activated receptor, gamma, coactivator 1, alpha (PPARGC1A), mRNA" 14 pages, Sep. 24, 2006.
GenBank® Accession No. NM_014046.3 (GI No. 186928836) "*Homo sapiens* mitochondrial ribosomal protein S18B (MRPS18B), nuclear gene encoding mitochondrial protein, mRNA" 4 pages, Mar. 13, 2011.
GenBank® Accession No. NM_014236.3 (GI No. 170650722) "*Homo sapiens* glyceronephosphate O-acyltransferase (GNPAT), mRNA" 4 pages, Mar. 11, 2011.
GenBank® Accession No. NM_016034.4 (GI No. 389565494) "*Homo sapiens* mitochondrial ribosomal protein S2 (MRPS2), nuclear gene encoding mitochondrial protein, mRNA" 3 pages, Mar. 10, 2011.
GenBank® Accession No. NM_016070.3 (GI No. 312222785) "*Homo sapiens* mitochondrial ribosomal protein S23 (MRPS23), nuclear gene encoding mitochondrial protein, mRNA" 3 pages, Mar. 13, 2011.
GenBank® Accession No. NM_016335.4 (GI No. 304766735) "*Homo sapiens* proline dehydrogenase (oxidase) 1 (PRODH), nuclear gene encoding mitochondrial protein, transcript variant 1, mRNA" 5 pages, Mar. 11, 2011.
GenBank® Accession No. NM_022061.3 (GI No. 169403966) "*Homo sapiens* mitochondrial ribosomal protein L17 (MRPL17), nuclear gene encoding mitochondrial protein, mRNA" 4 pages, Mar. 12, 2011.
GenBank® Accession No. NM_058165.1 (GI No. 148746190) "*Homo sapiens* monoacylglycerol O-acyltransferase 1 (MOGAT1), mRNA" 2 pages, Jun. 3, 2007.
GenBank® Accession No. NM_133263.2 (GI No. 289577087) "*Homo sapiens* peroxisome proliferator-activated receptor gamma, coactivator 1 beta (PPARGC1B), mRNA" 4 pages, Feb. 14, 2010.
GenBank® Accession No. NM_173158.1 (GI No. 320202954) "*Homo sapiens* nuclear receptor subfamily 4, group A, member 1 (NR4A1), transcript variant 3, mRNA" 3 pages, Feb. 18, 2007.
GenBank® Accession No. NM_182640.2 (GI No. 186910309) "*Homo sapiens* mitochondrial ribosomal protein S9 (MRPS9), nuclear gene encoding mitochondrial protein, mRNA" 4 pages, Mar. 12, 2011.
GenBank® Accession No. NP_000089.1 (GI No. 4503023) "carnitine O-palmitoyltransferase 2, mitochondrial precursor [*Homo sapiens*]" 3 pages, Mar. 12, 2011.
GenBank® Accession No. NP_001104753.1 (GI No. 163659899) "insulin-like growth factor I isoform 1 preproprotein [*Homo sapiens*]" Mar. 23, 2014, 3 pages.
GenBank® Accession No. NP_001119594.1 (GI No. 186928860) "mitochondrial thiamine pyrophosphate carrier [*Homo sapiens*]" 3 pages, Mar. 12, 2011.
GenBank® Accession No. NP_001177990.1 (GI No. 300796991) "mitochondrial glutamate carrier 1 [*Homo sapiens*]" 2 pages, Mar. 11, 2011.
GenBank® Accession No. NP_002006.2 (GI No. 9257222) "forkhead box protein O1 [*Homo sapiens*]" 3 pages, Mar. 13, 2011.
GenBank® Accession No. NP_002075.2 (GI No. 6006001) "glutathione peroxidase 3 precursor [*Homo sapiens*]" Mar. 16, 2014, 3 pages.
GenBank® Accession No. NP_002323.2 (GI No. 126012562) "prolow-density lipoprotein receptor-related protein 1 precursor [*Homo sapiens*]" Feb. 22, 2014, 7 pages.
GenBank® Accession No. NP_002534.1 (GI No. 4505501) "oxidized low-density lipoprotein receptor 1 isoform 1 [*Homo sapiens*]" 3 pages, Mar. 20, 2011.
GenBank® Accession No. NP_002602.2 (GI No. 19923736) "pyruvate dehydrogenase kinase, isozyme 2 isoform 1 precursor [*Homo sapiens*]" 3 pages, Mar. 11, 2011.
GenBank® Accession No. NP_004125.3 (GI No. 24234688) "stress-70 protein, mitochondrial precursor [*Homo sapiens*]" Feb. 27, 2014, 4 pages.
GenBank® Accession No. NP_005975.1 (GI No. 21389315) "tricalboxylate transport protein, mitochondrial precursor [*Homo sapiens*]" 3 pages, Mar. 13, 2011.
GenBank® Accession No. NP_006558.1 (GI No. 5729820) "phenylalanyl-tRNA synthetase, mitochondrial precursor [*Homo sapiens*]" 3 pages, Mar. 10, 2011.
GenBank® Accession No. NP_009120.1 (GI No. 27881506) "ATP-binding cassette sub-family F member 2 isoform a [*Homo sapiens*]" 3 pages, Mar. 12, 2011.
GenBank® Accession No. NP_031399.2 (GI No. 41281398) "leucine-rich repeat protein SHOC-2 isoform 1 [*Homo sapiens*]," Mar. 2, 2014, 5 pages.
GenBank® Accession No. NP_033360.2 (GI No. 34485724) "*Homo sapiens* Kirsten rat sarcoma viral oncogene homolog (KRAS), transcript variant a, mRNA," Jan. 11, 2014, 7 pages.
GenBank® Accession No. NP_037393.1 (GI No. 7019499) "peroxisome proliferator-activated receptor gamma coactivator 1-alpha [*Homo sapiens*]" 3 pages, Mar. 25, 2011.

(56) References Cited

OTHER PUBLICATIONS

GenBank® Accession No. NP_055051.1 (GI No. 7657134) "dihydroxyacetone phosphate acyltransferase [*Homo sapiens*]" 3 pages, Mar. 11, 2011.
GenBank® Accession No. NP_057154.2 (GI No. 16554604) "28S ribosomal protein S23, mitochondrial [*Homo sapiens*]" 2 pages, Mar. 13, 2011.
GenBank® Accession No. NP_116130.2 (GI No. 15100175) "1-acyl-sn-glycerol-3-phosphate acyltransferase alpha [*Homo sapiens*]" 3 pages, Mar. 11, 2011.
GenBank® Accession No. NP_203524.1 (GI No. 15718763) "GTPase KRas isoform a [*Homo sapiens*]," Mar. 16, 2014, 4 pages.
GenBank® Accession No. NP_477513.2 (GI No. 148746191) "2-acylglycerol O-acyltransferase 1 [*Homo sapiens*]" 2 pages, Dec. 26, 2010.
GenBank® Accession No. XM_005253365.1 (GI No. 530399132) "Predicted: *Homo sapiens* Kirsten rat sarcoma viral oncogene homolog (KRAS), transcript variant X1, mRNA" Aug. 13, 2013, 2 pages.
GenBank® Accession No. XM_005257266.1 (GI No. 530412017) "Predicted: *Homo sapiens* acetyl-CoA carboxylase alpha (ACACA), transcript variant X1, mRNA" 4 pages, Aug. 13, 2013.
GenBank® Accession No. XM_005263503.1 (GI No. 530360654) "Predicted: *Homo sapiens* solute carrier family 25 (pyrimidine nucleotide carrier), member 33 (SLC25A33), transcript variant X1, mRNA" 2 pages, Aug. 13, 2013.
GenBank® Accession No. XM_005267052.1 (GI No. 530383869) "Predicted: *Homo sapiens* acylglycerol-3-phosphate O-acyltransferase 4 (AGPAT4), transcript variant X1, mRNA" 3 pages, Aug. 13, 2013.
GenBank® Accession No. XP_005253422.1 (GI No. 530399133) "Predicted: GTPase KRas isoform X1 [*Homo sapiens*]" Aug. 13, 2013, 2 pages.
GenBank® Accession No. XP_005263560.1 (GI No. 530360655) "Predicted: solute carrier family 25 member 33 isoform X1 [*Homo sapiens*]" 1 page, Aug. 13, 2013.
Goffin and Zbuk, "Epidermal growth factor receptor: pathway, therapies, and pipeline," *Clin Ther.*, 35(9):1282-1303, Sep. 2013.
Gutscher et al., "Proximity-based protein thiol oxidation by H2O2-scavenging peroxidases," *J Biol Chem.*, 284(46):31532-31540, Epub Sep. 15, 2009.
Hatzivassiliou et al., "Mechanism of MEK inhibition determines efficacy in mutant KRAS-versus BRAF-driven cancers," *Nature*, 501(7466):232-236, Epub Aug. 11, 2013.
Huang et al., "Pleurotus tuber-regium Polysaccharides Attenuate Hyperglycemia and Oxidative Stress in Experimental Diabetic Rats," *Evid Based Complement Alternat Med.*, 2012:856381, Epub Aug. 30, 2012.
Iablokov et al., "Naturally occurring glycoalkaloids in potatoes aggravate intestinal inflammation in two mouse models of inflammatory bowel disease," *Dig Dis Sci.*, 55(11):3078-3085, Epub Mar. 3, 2010.
Ikeuchi et al., Overexpression of mitochondrial transcription factor a ameliorates mitochondrial deficiencies and cardiac failure after myocardial infarction, *Circulation*, 112(5):683-690, Epub Jul. 25, 2005.
International Preliminary Report on Patentability for PCT/US2016/024295, dated Oct. 12, 2017, 10 pages.
International Search Report and Written Opinion for PCT/US2016/024295, dated Jun. 27, 2016, 11 pages.
Jaeger and Pietrzik, "Functional role of lipoprotein receptors in Alzheimer's disease," *Curr Alzheimer Res.*, 5(1):15-25, Feb. 2008.
Jongmans et al., "Noonan syndrome, the SOS1 gene and embryonal rhabdomyosarcoma," *Genes Chromosomes Cancer*, 49(7):635-641, Jul. 2010.
Ju et al., "Anti-obesity and antioxidative effects of purple sweet potato extract in 3T3-L1 adipocytes in vitro," *J Med Food.*, 14(10):1097-1106, Epub Aug. 23, 2011.
Kakimoto et al., "Automated recognition and quantification of pancreatic islets in Zucker diabetic fatty rats treated with exendin-4," *J Endocrinol.*, 216(1):13-20, Jan. 2, 2013.

Kang et al., "Mitochondrial transcription factor A (TFAM): roles in maintenance of mtDNA and cellular functions," *Mitochondrion*, 7(1-2):39-44, Epub Dec. 8, 2006.
Kodamatani et al., "Simple and sensitive method for determination of glycoalkaloids in potato tubers by high-performance liquid chromatography with chemiluminescence detection," *J Chromatogr A.*, 1100(1):26-31, Epub Sep. 27, 2005.
Köhler and Schuler, "Afatinib, erlotinib and gefitinib in the first-line therapy of EGFR mutation-positive lung adenocarcinoma: a review," *Onkologie*, 36(9):510-518, Epub Aug. 19, 2013.
Kovalevich and Langford, "Considerations for the use of SH-SY5Y neuroblastoma cells in neurobiology," *Methods Mol Biol.*, 1078:9-21, 2013.
Kummer et al., "Nitric oxide decreases the enzymatic activity of insulin degrading enzyme in APP/PS1 mice," *J Neuroimmune Pharmacol.*, 7(1):165-172, Epub Jan. 8, 2012.
Kusano and Abe, "Antidiabetic activity of white skinned sweet potato (*Ipomoea batatas* L.) in obese Zucker fatty rats," *Biol Pharm Bull.*, 23(1):23-26, Jan. 2000.
Langkilde et al., "A 28-day repeat dose toxicity study of steroidal glycoalkaloids, alpha-solanine and. alpha-chaconine in the Syrian Golden hamster," *Food Chem Toxicol.*, 47(6):1099-1108, Epub Feb. 13, 2009.
Lee et al., "Dysregulation of adipose glutathione peroxidase 3 in obesity contributes to local and systemic oxidative stress," *Mol Endocrinol.*, 22(9):2176-2189, Epub Jun. 18, 2008.
Li et al., "Effect of the Lycium barbarum polysaccharides on age-related oxidative stress in aged mice," Journal of Ethnopharmacology, 2007, 111(28):504-511.
Li et al., "Insulin and insulin-like growth factor-I receptors differentially mediate insulin-stimulated adhesion molecule production by endothelial cells," *Endocrinology*, 150(8):3475-3482, Epub May 7, 2009.
Li et al., "Lycium Barbarum Polysaccharides Reduce Neuronal Damage, Blood-Retinal Barrier Disruption and Oxidative Stress in Retinal Ischemia/Reperfusion Injury," PLoS One, 2011, 6(1):e16380, 14 pages.
Love et al., "The relationship between human skeletal muscle pyruvate dehydrogenase phosphatase activity and muscle aerobic capacity," *J Appl Physiol* (1985), 111(2):427-434, Epub May 19, 2011.
Lu et al., "α-Solanine inhibits human melanoma cell migration and invasion by reducing matrix metalloproteinase-2/9 activities," *Biol Pharm Bull.*, 33(10):1685-1691, 2010.
Ludvik et al., "Efficacy of Ipomoea batatas (Caiapo) on diabetes control in type 2 diabetic subjects treated with diet," *Diabetes Care*, 27(2):436-440, Feb. 2004.
Ludvik et al., "Mode of action of ipomoea batatas (caiapo) in type 2 diabetic patients," *Metabolism XX US.*, 52(7):875-880, Jul. 1, 2003.
Mandimika et al., "Differential gene expression in intestinal epithelial cells induced by single and mixtures of potato glycoalkaloids," *J Agric Food Chem.*, 28;55(24):10055-10066, Epub Nov. 1, 20007.
Mantione et al., "Endogenous morphine signaling via nitric oxide regulates the expression of CYP2D6 and COMT: autocrine/paracrine feedback inhibition," *Addict Biol.*, 13(1):118-123, Epub Jun. 16, 2007.
Mantione et al., "Identification of a μ opiate receptor signaling mechanism in human placenta," *Med Sci Monit.*, 16(11):BR347-BR352, Nov. 2010.
Martin et al., "KRAS mutations as prognostic and predictive markers in non-small cell lung cancer," *J Thorac Oncol.*, 8(5):530-542, May 2013.
Matsuda et al., "Determination of potato glycoalkaloids using high-pressure liquid chromatography-electrospray ionisation/mass spectrometry," *Phytochem Anal.*, 15(2):121-124, Mar.-Apr. 2004.
McClelland et al., "Bio-medical effect of Sweet Potato in People with Diabetes," *J Am Dietetic Association.*, 107(8): A104, Jul. 24, 2007.
McGehee et al., "Cholinesterase inhibition by potato glycoalkaloids slows mivacurium metabolism," *Anesthesiology.*, 93(2):510-519, Aug. 2000.

(56) References Cited

OTHER PUBLICATIONS

McLoughlin and Miller, "The FE65 proteins and Alzheimer's disease," *J Neurosci Res.*, 86(4):744-754, Mar. 2008.
Miners et al., "Aβ-degrading enzymes: potential for treatment of Alzheimer disease," *J Neuropathol Exp Neurol.*, 70(11):944-959, Nov. 2011.
Minuti et al., "Targeted therapy for NSCLC with driver mutations," *Expert Opin Biol Ther.*, 13(10):1401-1412, Oct. 2013.
Murray, Encyclopedia of Nutritional Supplements, pp. 44-53 and pp. 343-346, 1996.
Nakajima et al., "Potato extract (Potein) suppresses food intake in rats through inhibition of luminal trypsin activity and direct stimulation of cholecystokinin secretion from enteroendocrine cells," *J Agric Food Chem.*, 59(17):9491-9496, Epub Aug. 16, 2011.
Neant-Fery et al., "Molecular basis for the thiol sensitivity of insulin-degrading enzyme," *Proc Natl Acad Sci U S A.*, 105(28):9582-9587, Epub Jul. 8, 2008.
Oki et al., "The effects of an arabinogalactan-protein from the white-skinned sweet potato (*Ipomoea batatas* L.) on blood glucose in spontaneous diabetic mice," *Biosci Biotechnol Biochem.*, 75(3):596-598, Feb. 1, 2012.
Otto et al., "Longitudinal study of painful diabetic neuropathy in the Zucker diabetic fatty rat model of type 2 diabetes: impaired basal G-protein activity appears to underpin marked morphine hyposensitivity at 6 months," *Pain Med.*, 12(3):437-50. Epub Feb. 18, 2011.
Pandini et al., "Insulin has multiple antiamyloidogenic effects on human neuronal cells," *Endocrinology*, 154(1):375-387, Epub Dec. 13, 2012.
Pollio et al., "Increased expression of the oligopeptidase THOP1 is a neuroprotective response to Abeta toxicity," *Neurobiol Dis.*, 31(1):145-158, Epub Apr. 29, 2008.
Robertson et al., "The frequency of KRAS and BRAF mutations in intrahepatic cholangiocarcinomas and their correlation with clinical outcome," *Hum Pathol.*, 44(12):2768-2773, Epub Oct. 15, 2013.
Rolyan et al., "Amyloid-β protein modulates the perivascular clearance of neuronal apolipoprotein E in mouse models of Alzheimer's disease," *J Neural Transm.*, 118(5):699-712, Epub Jan. 6, 2011.
Ruprich et al., "Probabilistic modelling of exposure doses and implications for health risk characterization: glycoalkaloids from potatoes," *Food Chem Toxicol.*, 47(12):2899-2905, Epub Mar. 13, 2009.
Sagare et al., "Low-density lipoprotein receptor-related protein 1: a physiological Aβ homeostatic mechanism with multiple therapeutic opportunities," *Pharmacol Ther.*, 136(1):94-105, Epub Jul. 20, 2012.
Schiepers et al., "APOE E4 status predicts age-related cognitive decline in the ninth decade: longitudinal follow-up of the Lothian Birth Cohort 1921," *Mol Psychiatry*, 17(3):315-324, Epub Jan. 25, 2011.
Shibue et al., "An integrin-linked machinery of cytoskeletal regulation that enables experimental tumor initiation and metastatic colonization," *Cancer Cell.*, 24(4):481-498, Epub Sep. 12, 2013.
Singh et al., "Protective effect of potato peel powder in ameliorating oxidative stress in streptozotocin diabetic rats," *Plant Foods Hum Nutr.*, 60(2):49-54, Jun. 2005.
Smith, J.G., Organic Chemistry, 3rd ed, McGaw Hill, 2009, p. 241.
Stentz and Kitabchi, "Transcriptome and proteome expression in activated human CD4 and CD8 T-lymphocytes," *Biochem Biophys Res Commun.*, 324(2):692-696, Nov. 12, 2004.
Stöhr and Federici, "Insulin resistance and atherosclerosis: convergence between metabolic pathways and inflammatory nodes," *Biochem J.*, 454(1):1-11, Aug. 15, 2013.
Stöhr et al., "Insulin receptor signaling mediates APP processing and β-amyloid accumulation without altering survival in a transgenic mouse model of Alzheimer's disease," *Age (Dordr).*, 35(1):83-101, Epub Nov. 6, 2011.
Sugden and Holness, "Therapeutic potential of the mammalian pyruvate dehydrogenase kinases in the prevention of hyperglycaemia," *Curr Drug Targets Immune Endocr Metabol Disord.*, 2(2):151-165, Jul. 2002.
Talaei et al., "Increased protein aggregation in Zucker diabetic fatty rat brain: identification of key mechanistic targets and the therapeutic application of hydrogen sulfide," *BMC Cell Biol.*, 15:1, 17 pages, Jan. 6, 2014.
Tan et al., "Regulation of mammalian pyruvate dehydrogenase alpha subunit gene expression by glucose in HepG2 cells," *Biochem J.*, 336 ( Pt 1):49-56, Nov. 15, 1998.
UniProtKB/Swiss-Prot: 000213.2 (GI No. 12229629) "RecName: Full=Amyloid beta A4 precursor protein-binding family B member 1; AltName: Full=Protein Fe65," Mar. 19, 2014, 12 pages.
Watt et al., "Bioenergetic cost of making an adenosine triphosphate molecule in animal mitochondria," *Proc Natl Acad Sci U S A.*, 107(39):16823-16827, Epub Sep. 16, 2010.
Weksler et al., "The immune system, amyloid-b peptide, and Alzheimer's disease," Immunological Reviews, 2005, 205:244-256.
Welters et al., "NF-kappaB, nitric oxide and opiate signaling," *Med Hypotheses.*, 54(2):263-268, Feb. 2000.
Yamatoya et al., "Hypolipidemic effects of hydrolyzed xyloglucan," *Macromolecular Symposia*, 120(1): 231-236, Jul. 1997.
Zanchi et al., "Renal expression of FGF23 in progressive renal disease of diabetes and the effect of ACE inhibitor," *PLoS One.*, 8(8):e70775, Aug. 14, 2013.
Zhu et al., "Cholinergic regulation of morphine release from human white blood cells: evidence for a novel nicotinic receptor via pharmacological and microarray analysis," *Int J Immunopathol Pharmacol.*, 20(2):229-237, Apr.-Jun. 2007.
Zywicki et al., "Comparison of rapid liquid chromatography-electrospray ionization-tandem mass spectrometry methods for determination of glycoalkaloids in transgenic field-grown potatoes," *Anal Biochem.*, 336(2):178-186, Jan. 15, 2005.
Japanese Office Action in Application No. JP2016-544345, dated Jul. 5, 2018, 6 pages (with English Translation).
Kumar et al., "Dietary roles of non-starch polysachharides in human nutrition: A Review," *Crit Rev Food Sci Nutr.*, 52(10/11):899-935, 2012.
Ohtani and Misaki., "An in vitro study of the effects of cell wall polysaccharides of potatoes on digestibilities of their starched," *Journal of the Japan Society of Nutrition and Food Science.*, 38(5):363-370, 1985.
Ohtani., "Structure of non-starchy polysaccharides of potatoes (*Solanum tuberosum*) having different cooking properties (Part 1)," *Journal of Home Economics of Japan.*, 40(7):593-601, 1989.
Ohtani., "Structure of non-starchy polysaccharides of potatoes (*Solanum tuberosum*) having different cooking properties (Part 2)," *Journal of Home Economics of Japan.*, 42(4):313-320, 1991.
Ohtani., "Structure of non-starchy polysaccharides of potatoes (*Solanum tuberosum*) having different cooking properties (Part 3)," *Journal of Home Economics of Japan.*, 42(4):321-325, 1991.
Proceedings of the 60th commemoration meeting of the Japanese Society for Food Science and Technology, Aug. 29, 2013, 124 (reference showing well-known technique).
U.S. Appl. No. 15/023,069, filed Mar. 18, 2016, 2016-0243152, Aug. 25, 2016, Stefano et al.
U.S. Appl. No. 15/472,559, filed Mar. 9, 2017, 2017-0232033, Aug. 17, 2017, Stefano et al.
U.S. Appl. No. 15/562,136, filed Sep. 27, 2017, 2018-0078599, Mar. 22, 2018, Stefano et al.
Extended European Search Report in Application No. 16773856.6, dated Oct. 2, 2018, 7 pages.
Yaoi., J Applied Glycoscience., 2(3):185-190, 2012.
Zykwinska et al., "Evidence for in vitro binding of pectin side chains to cellulose1," Plant Physiology., 139:397-407, Sep. 2005.
Ludvik et al, "Mode of action of ipomoea batatas (Caiapo) in type 2 diabetic patients," Metabolism, Jul. 2003, 52(7):875-80.
Vincken et al, "Potato xyloglucan is built from XXGG-type subunits," Carbohydrate Research, Jul. 19, 1996, 288:219-232.
Galactomannan, Wikipedia, [retrieved from internet on Apr. 29, 2019] <URL: https://en.wikipedia.org/wiki/Galactomannan> published on Apr. 26, 2013 as per Wayback Machine.
Jancik et al., "Clinical Relevance of KRAS in Human Cancers," J. Bionnedi. and Biotech., 2010:13, 2010.
Jarvis et al., "The polysaccharide structure of potato cell walls: chemical fractionation," Planta, 152(2):93-100, Jun. 1981.

(56) References Cited

OTHER PUBLICATIONS

Maxwell, "Effects of modified bioactive pectins on colon cancer cells in vitro," Thesis for Doctor of Philosophy, published 2014.

Ikeda, "Metabolic Turn Over of Amyloid Fibrils and Post-Treatment Regression of Amyloid Deposits in Systemic Amyloidosis With Polyneuropathy," Rinsho Shinkeigaku= Clinical neurology, 51(11):1143-5, Nov. 2011, (English abstract at the end of document).

Olmstead et al., "A summary of molecular systematic research in Solanaceae: 1982-2006," InVI International Solanaceae Conference: Genomics Meets Biodiversity 745, (pp. 255-268), Jul. 2006.

Sekijima et al., "Epidemiological and clinical aspects of non-hereditary systemic amyloidosis," Rinsho shinkeigaku= Clinical neurology, 51(11):1130-3, Nov. 2011, (English abstract at the end of document).

Takuma, "Mitochondrial Dysfunction and Apoptosis in Neurodegenerative Diseases," The Japanese Pharmacological Society, 127(5):349-54, May 2006 (Partial English translation).

* cited by examiner

METHODS AND MATERIALS FOR REDUCING AMYLOID BETA LEVELS WITHIN A MAMMAL

CROSS-REFERENCE TO RELATED APPLICATION

This application is a National Stage Application under 35 U.S.C. § 371 and claims the benefit of International Application No. PCT/US2016/024295, filed Mar. 25, 2016, which claims priority to U.S. Provisional Application No. 62/139,178, filed Mar. 27, 2015. The disclosures of the foregoing applications are hereby incorporated by reference in their entirety.

BACKGROUND

1. Technical Field

This document relates to methods and materials for reducing amyloid beta levels within a mammal having Alzheimer's disease. For example, this document relates to using compositions containing a potato polysaccharide preparation to reduce one or more symptoms of Alzheimer's disease. In some cases, this document relates to using compositions containing a potato polysaccharide preparation to degrade CNS-derived amyloid beta polypeptides.

2. Background Information

Potatoes are starchy, edible tubers obtained from potato plants and form an integral part of much of the world's food supply. In fact, potatoes are the fourth largest food crop in the world. The main potato species worldwide is *Solanum tuberosum*.

SUMMARY

This document provides methods and materials for reducing amyloid beta levels within a mammal (e.g., a mammal having Alzheimer's disease). For example, this document provides methods for using compositions containing a potato polysaccharide preparation to reduce one or more symptoms of Alzheimer's disease. In some cases, a composition containing a potato polysaccharide preparation provided herein can be used to increase binding, sequestration, and/or degradation of CNS-derived amyloid beta polypeptides. In some cases, a composition containing a potato polysaccharide preparation provided herein can be used degrade CNS-derived amyloid beta polypeptides, for example at peripheral sites of action and/or to inhibit the formation of neurofibrillary plaques.

Having the ability to use a composition containing a potato polysaccharide preparation described herein to reduce one or more symptoms of Alzheimer's disease can provide clinicians and patients with an effective treatment regime for improving a patient's quality of life.

This document also provides compositions (e.g., nutritional supplement compositions) that contain a potato polysaccharide preparation. For example, this document provides nutritional supplement compositions containing a potato polysaccharide preparation, methods for obtaining potato polysaccharide preparations, methods for making nutritional supplement compositions containing a potato polysaccharide preparation, and methods for increasing or decreasing expression of polypeptides involved with Alzheimer's disease.

In some cases, the compositions provided herein (e.g., nutritional supplement compositions and potato polysaccharide preparations provided herein) can be used to increase or decrease expression of polypeptides involved with Alzheimer's disease and the metabolism of CNS-derived amyloid beta polypeptides. For example, a composition containing a potato polysaccharide preparation provided herein or a potato polysaccharide preparation provided herein can be used to increase expression of a low density lipoprotein receptor-related protein 1 (LRP1) polypeptide, an amyloid beta (A4) precursor protein binding, family B member 1, (APBB1) polypeptide, an insulin degrading enzyme (IDE) polypeptide, a glutathione peroxidase 3 (GPX3) polypeptide, a glutathione peroxidase 4 (GPX4) polypeptide, or a combination thereof. In some cases, a composition containing a potato polysaccharide preparation provided herein or a potato polysaccharide preparation provided herein can be used to decrease expression of an insulin-like growth factor 1 (IGF1), a nitric oxide synthase 2, inducible (NOS2), or a combination thereof.

In some cases, the compositions provided herein (e.g., nutritional supplement compositions and potato polysaccharide preparations provided herein) can be used to increase or decrease expression of polypeptides involved with binding, sequestration, and/or degradation of CNS-derived amyloid beta polypeptides in adipose tissue. For example, a composition containing a potato polysaccharide preparation provided herein or a potato polysaccharide preparation provided herein can be used to increase expression of an LRP1 polypeptide, an APBB1 polypeptide, an IDE polypeptide, a GPX3 polypeptide, or a combination thereof.

In some cases, the compositions provided herein (e.g., nutritional supplement compositions and potato polysaccharide preparations provided herein) can be used to increase or decrease expression of polypeptides involved with binding, sequestration, and/or degradation of CNS-derived amyloid beta polypeptides in blood. For example, a composition containing a potato polysaccharide preparation provided herein or a potato polysaccharide preparation provided herein can be used to increase expression of an APBB1 polypeptide, an IDE polypeptide, a GPX4 polypeptide, or a combination thereof.

In some cases, the compositions provided herein (e.g., nutritional supplement compositions and potato polysaccharide preparations provided herein) can be used to increase or decrease expression of polypeptides involved with oxidative stress and proinflammatory pathways. For example, a composition containing a potato polysaccharide preparation provided herein or a potato polysaccharide preparation provided herein can be used to decrease expression of an insulin-like growth factor 1 (IGF1) polypeptide, a nitric oxide synthase 2, inducible (NOS2) polypeptide, or a combination thereof.

In general, one aspect of this document features a method for reducing amyloid beta levels within a mammal having Alzheimer's disease. The method comprises, or consist essentially of, administering to the mammal a composition comprising a potato polysaccharide preparation obtained from raw potatoes, wherein the level of amyloid beta within the mammal is reduced. The mammal can be a human. The level of amyloid beta within the mammal can be reduced in blood. The level of amyloid beta within the mammal can be reduced in adipose tissue. The composition can comprise the potato polysaccharide preparation in an amount that results in between 0.05 mg and 50 mg of the potato polysaccharide component of the potato polysaccharide preparation being administered to the mammal per kg of body weight of the mammal. The composition can comprise between 1 mg and 100 mg of the potato polysaccharide preparation. The composition can comprise between 6 mg and 20 mg of the potato polysaccharide preparation. The composition can comprise between 1 mg and 100 mg of the potato polysaccharide component of the potato polysaccharide preparation. The composition can comprise between 6 mg and 20 mg of the potato polysaccharide component of the potato polysaccharide preparation. The composition can be in the form of a tablet. The composition can comprise alpha lipoic acid. The composition can comprise alpha tocopherol. The potato polysaccharide preparation can be in an amount that results in between 0.075 mg and 0.5 mg of the potato polysaccharide component of the potato polysaccharide preparation being administered to the mammal per kg of body weight of the mammal. At least about 80 percent of the potato polysaccharide preparation can be potato polysaccharide. At least about 90 percent of the potato polysaccharide preparation can be potato polysaccharide. At least about 95 percent of the potato polysaccharide preparation can be potato polysaccharide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
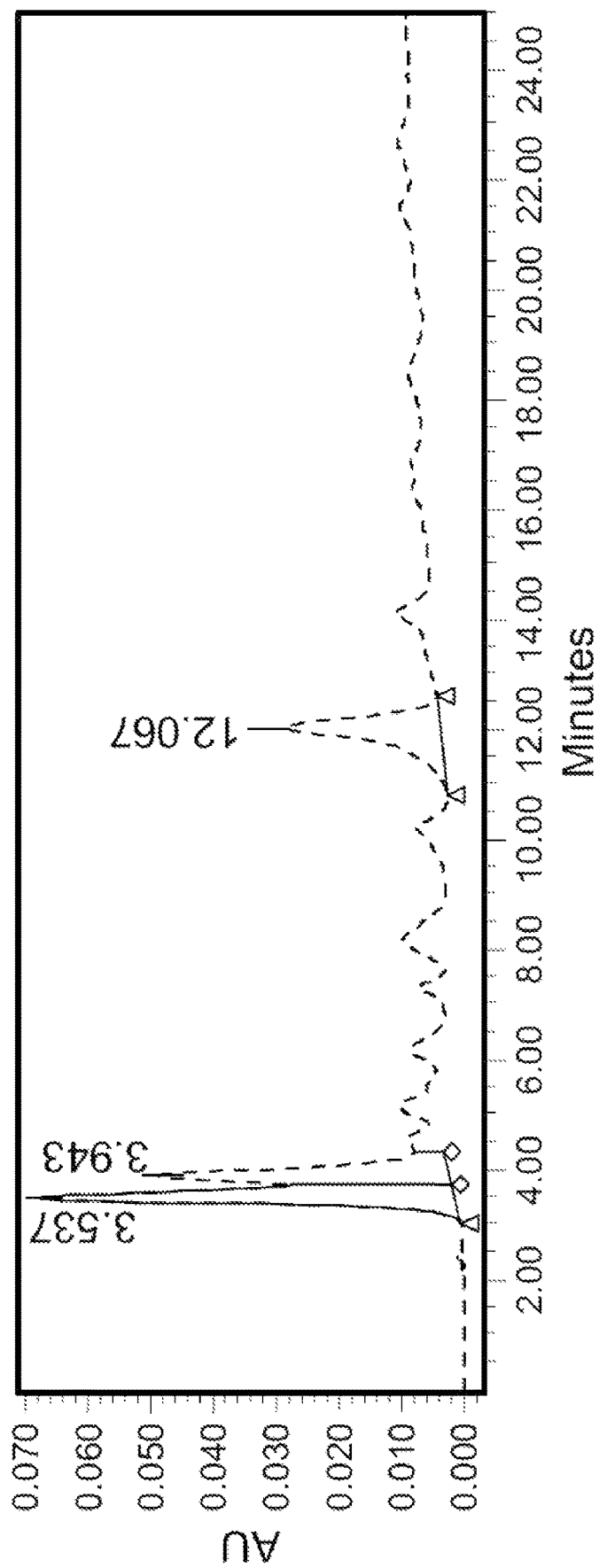
FIG. 1 is an HPLC chromatogram of a 10% ACN extract of raw potato (Russet Burbank).

This document provides methods and materials for reducing amyloid beta levels within a mammal (e.g., a mammal having Alzheimer's disease). As described herein, a composition containing a potato polysaccharide preparation can be used to reduce one or more symptoms of Alzheimer's disease. For example, a composition containing a potato polysaccharide preparation provided herein can be administered to any appropriate mammal (e.g., rat, mouse, dog, cat, horse, cow, goat, pig, chicken, duck, rabbit, sheep, monkey, or human) to reduce one or more symptoms of Alzheimer's disease. Examples of Alzheimer's disease symptoms include, without limitation, difficulty in remembering recent events (e.g., short term memory loss), problems with language, disorientation (including easily getting lost), mood swings, loss of motivation, not managing self-care, behavioral issues, or combinations thereof.

Any appropriate route of administration (e.g., oral or parenteral administration) can be used to administer a composition containing a potato polysaccharide preparation provided herein (e.g., a nutritional supplement composition provided herein) to a mammal. For example, a composition containing a potato polysaccharide preparation provided herein can be administered orally. In some cases, a composition containing a potato polysaccharide preparation provided herein can be administered by injection.

A composition provided herein (e.g., a nutritional supplement composition) can include one or more potato polysaccharide preparations. A potato polysaccharide preparation can be a preparation that is obtained from a water extract of potato and that contains polysaccharide material having the ability to be eluted from a C18 cartridge (e.g., a Sep-Pak Plus C-18 cartridge) with 10% acetonitrile. In some cases, a potato polysaccharide preparation can be a preparation that is obtained from potato and that contains polysaccharide material having HPLC characteristics of that of the peak eluted at 3.5 minutes as described in Example 1 (see, also, FIGS. 1, 2, and 27-33). In some cases, a polysaccharide of a potato polysaccharide preparation provided herein can be a polar, water-soluble polysaccharide. In some cases, a polysaccharide of a potato polysaccharide preparation provided herein can be a highly substituted complex xyloglucan material.

In some cases, a potato polysaccharide preparation can be a preparation that is obtained from potato and that contains polysaccharide material that, when derivatized, results in at least the following acylated carbohydrates as assessed using GC/MS: (a) myo-inositol (set to 1× to serve as an internal standard), (b) glucose at about 40× to about 60× the myo-inositol content (e.g., glucose at about 50× the myo-inositol content), (c) xylose at about 10× to about 20× the myo-inositol content (e.g., xylose at about 15× the myo-inositol content), (d) mannose at about 5× to about 15× the myo-inositol content (e.g., mannose at about 10× the myo-inositol content), and (e) galactose at about 3× to about 7× the myo-inositol content (e.g., galactose at about 5× the myo-inositol content). The derivatization procedure can include forming a dry residue of the polysaccharide material that is then hydrolyzed using trifluoroacetic acid. The resulting material is then reduced using sodium borohydride, and after borate removal, the end product is acylated using acetic anhydride and pyridine. The end products of the reaction are then injected directly on GC/MS to identify the acylated carbohydrates.

Figure 6:
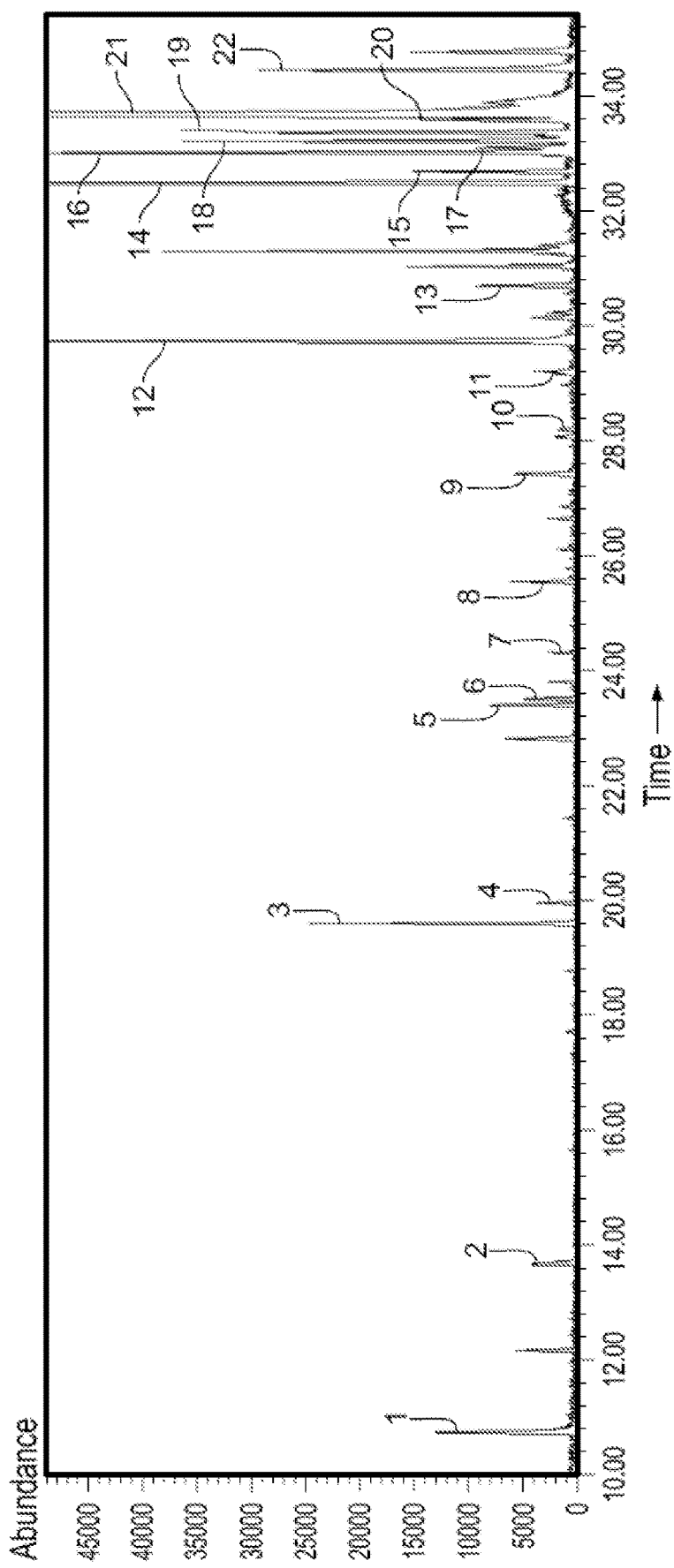
FIG. 6 is a total ion chromatogram of derivatized carbohydrate fragments of 3.5 minute HPLC peak material obtained from raw potato Russet Burbank).
Figure 7:
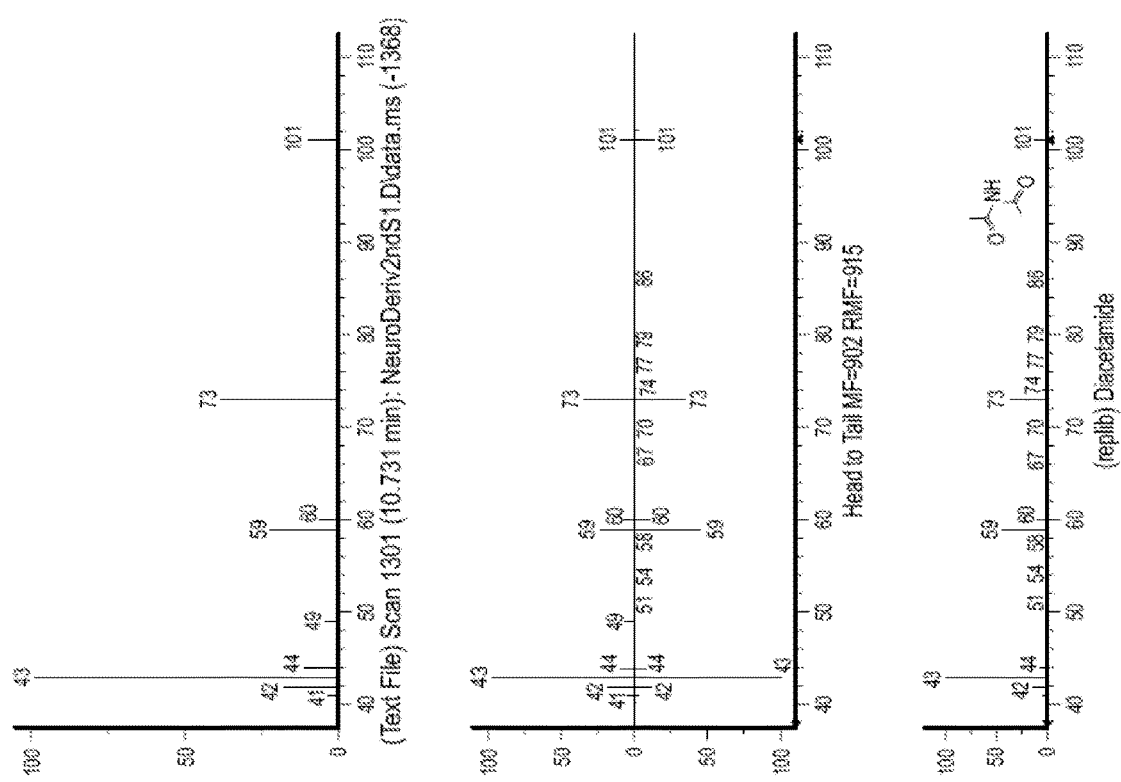
FIG. 7 is a fragmentation pattern of diacetamide. The peak fragmentation pattern is in the top panel, the compound library fragmentation match is in the bottom panel, and an overlay of the two is in the center panel.
Figure 8:
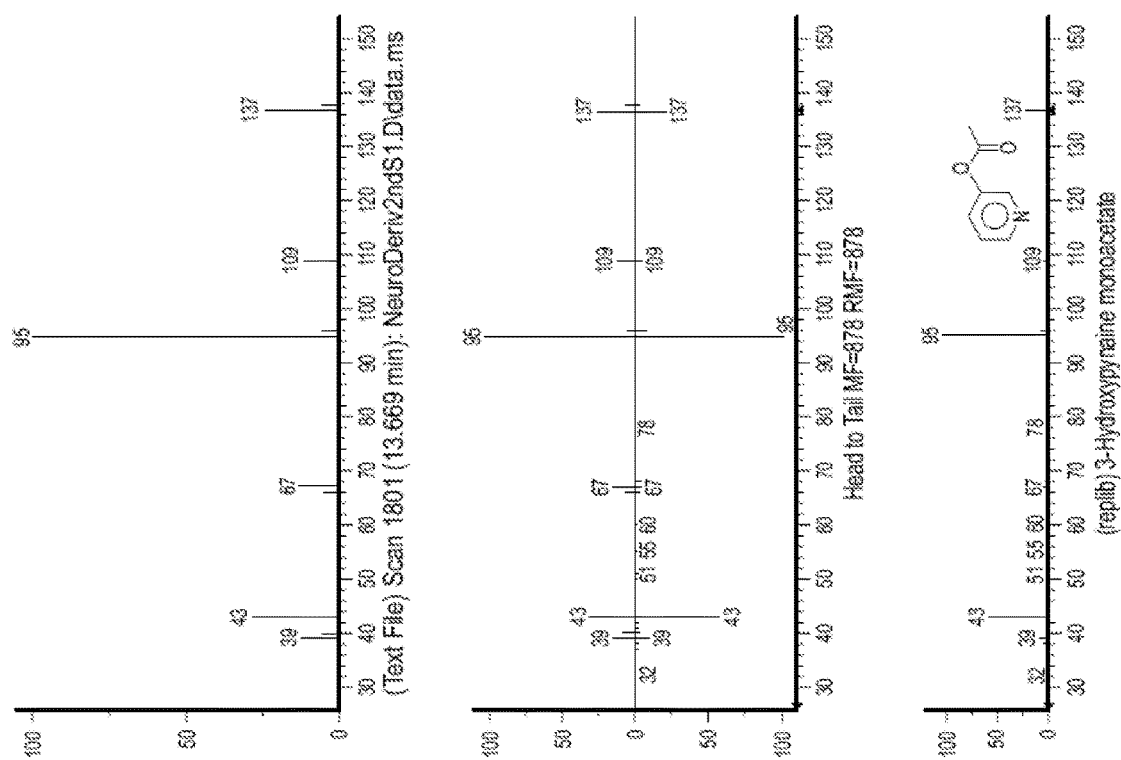
FIG. 8 is a fragmentation pattern of 3-acetoxy pyridine. The peak fragmentation pattern is in the top panel, the compound library fragmentation match is in the bottom panel, and an overlay of the two is in the center panel.
Figure 9:
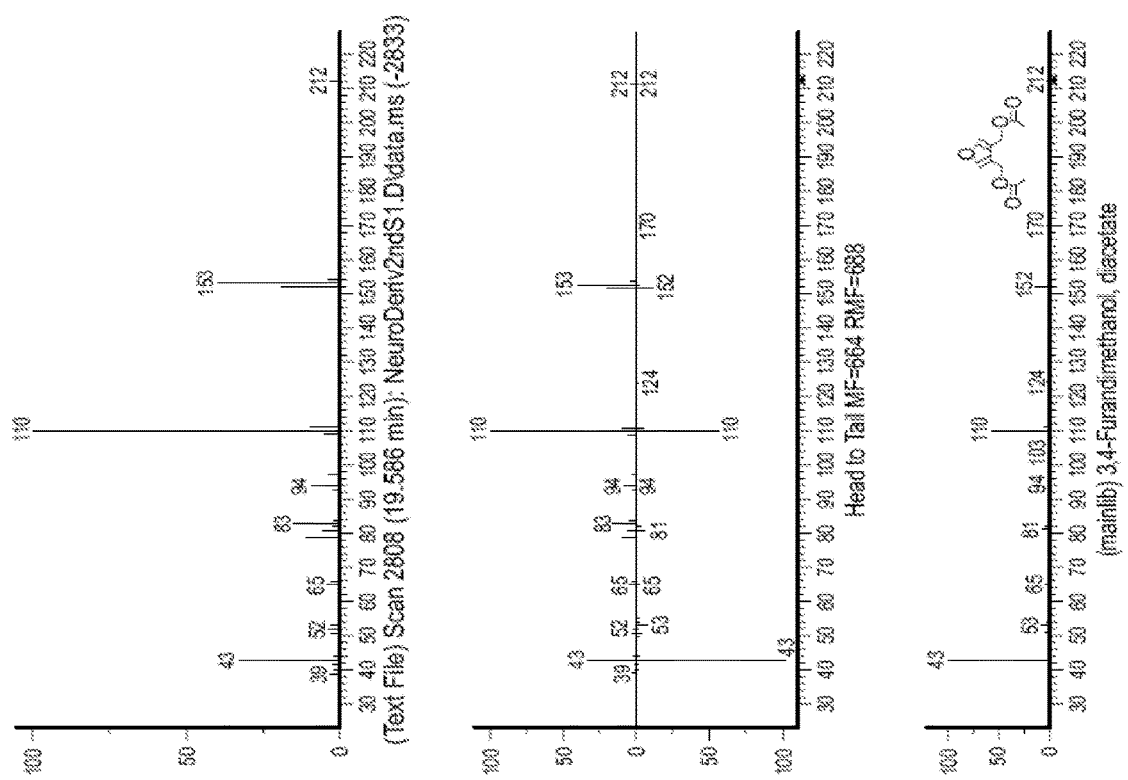
FIG. 9 is a fragmentation pattern of 3,4-furan dimethanol, diacetate. The peak fragmentation pattern is in the top panel, the compound library fragmentation match is in the bottom panel, and an overlay of the two is in the center panel.
Figure 10:
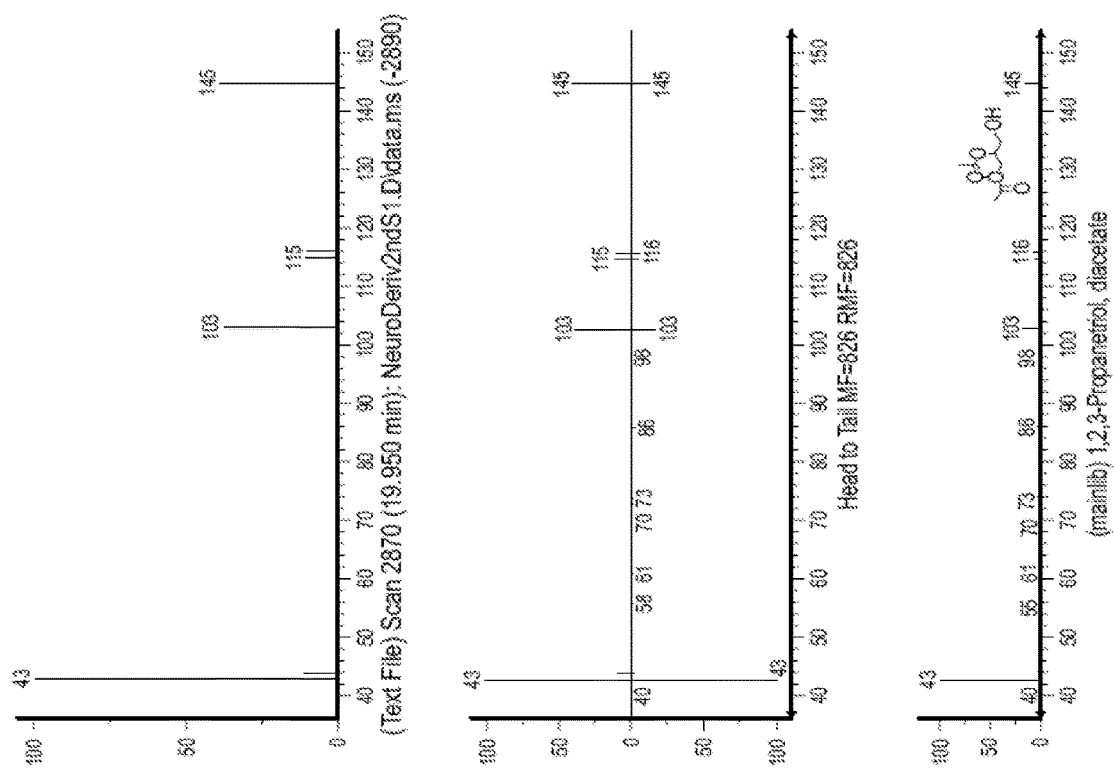
FIG. 10 is a fragmentation pattern of 1,2,3-propanetriol diacetate. The peak fragmentation pattern is in the top panel, the compound library fragmentation match is in the bottom panel, and an overlay of the two is in the center panel.
Figure 11:
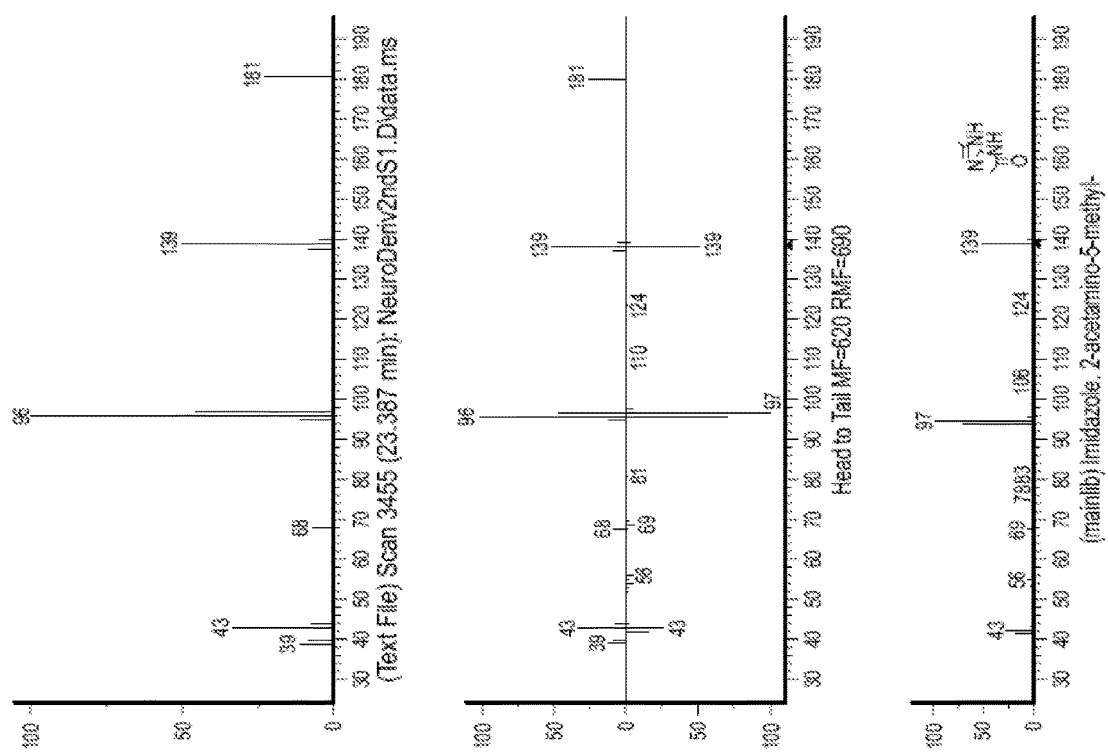
FIG. 11 is a fragmentation pattern of imidazole, 2-acetamino-5-methyl. The peak fragmentation pattern is in the top panel, the compound library fragmentation match is in the bottom panel, and an overlay of the two is in the center panel.
Figure 12:
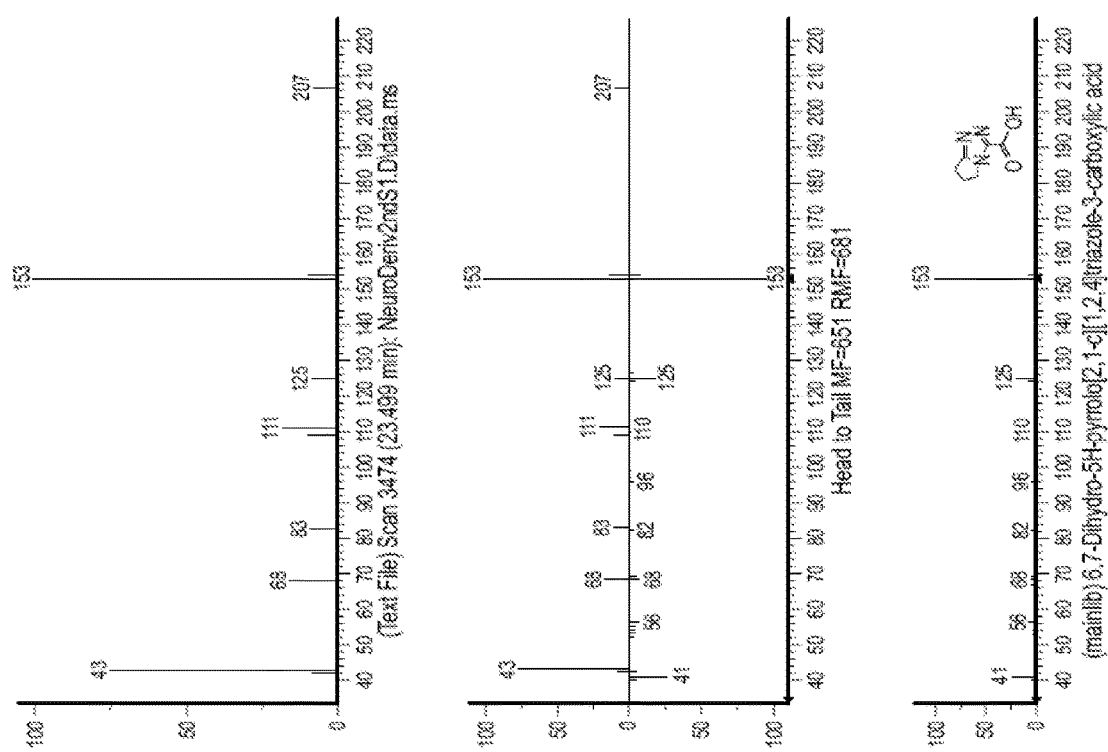
FIG. 12 is a fragmentation pattern of 6,7-dihydro-5H-pyrrol[2,1,c][1,2,4] triazole-3-carboxylic acid. The peak fragmentation pattern is in the top panel, the compound library fragmentation match is in the bottom panel, and an overlay of the two is in the center panel.
Figure 13:
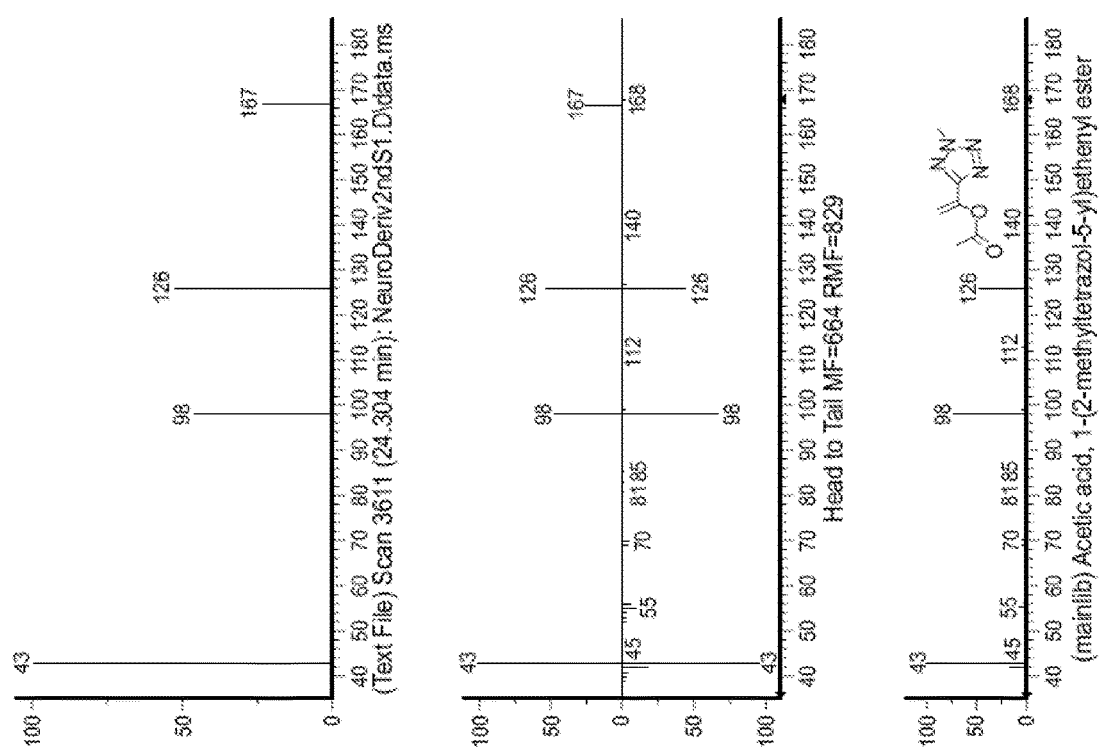
FIG. 13 is a fragmentation pattern of acetic acid, 1-(2-methyltetrazol-5-yl) ethenyl ester. The peak fragmentation pattern is in the top panel, the compound library fragmentation match is in the bottom panel, and an overlay of the two is in the center panel.
Figure 14:
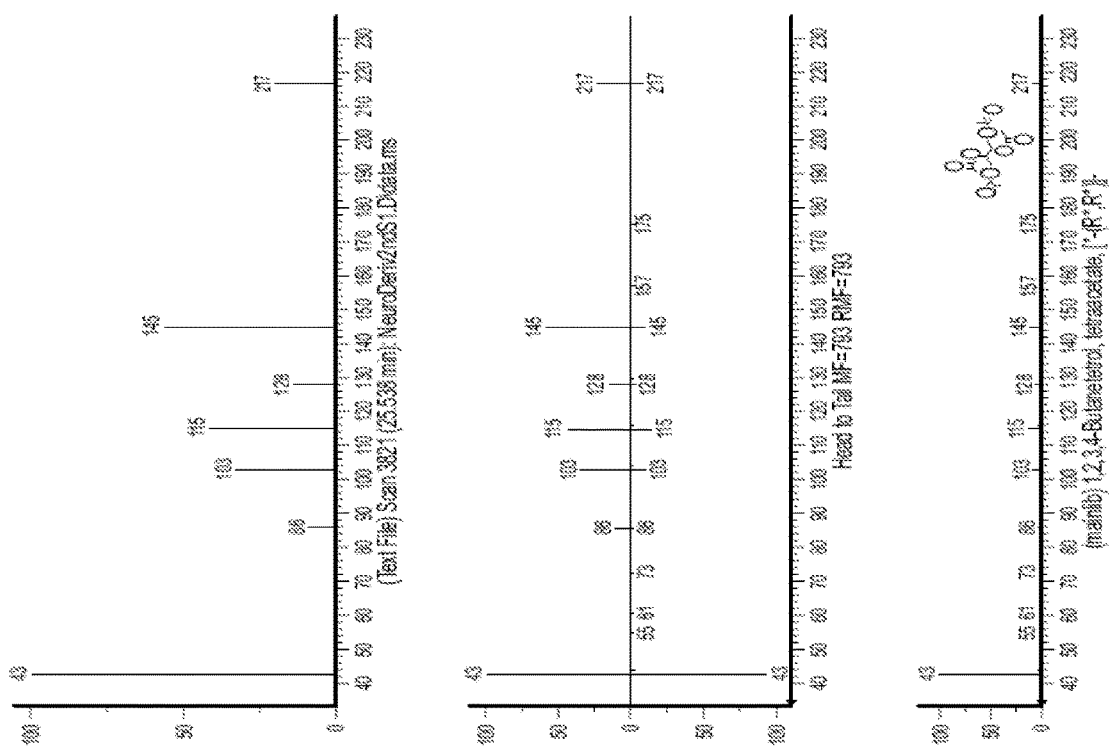
FIG. 14 is a fragmentation pattern of 1,2,3,4-butanetriol, tetraacetate (isomer 1). The peak fragmentation pattern is in the top panel, the compound library fragmentation match is in the bottom panel, and an overlay of the two is in the center panel.
Figure 15:
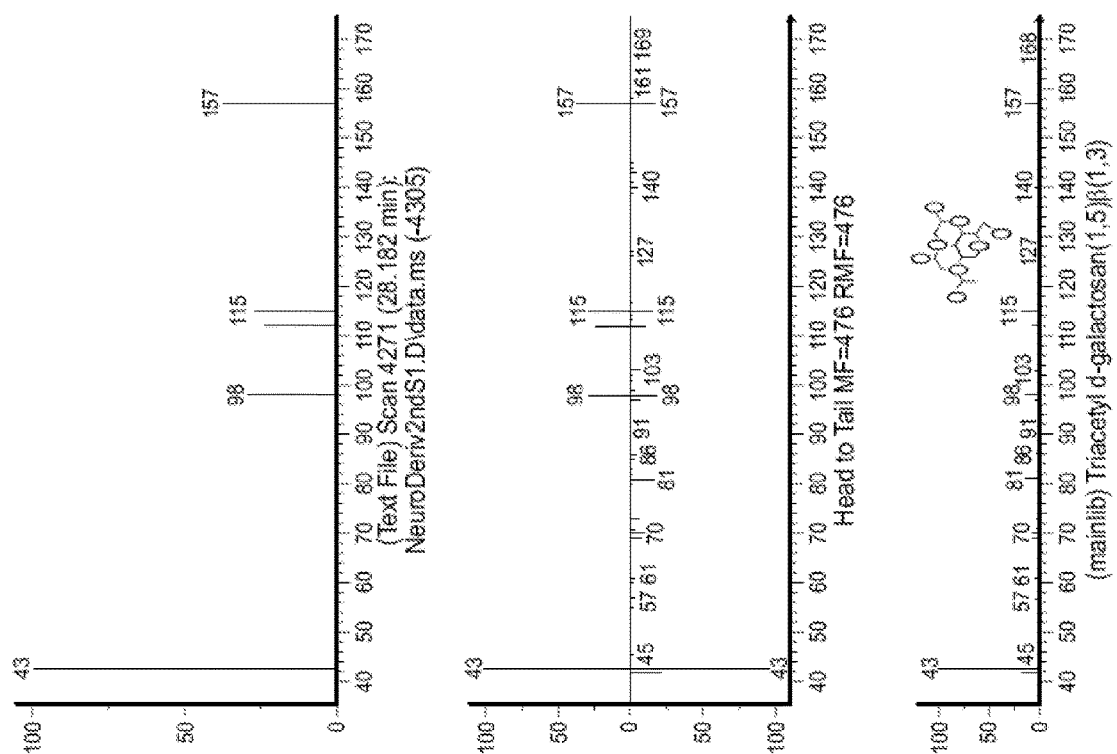
FIG. 15 is a fragmentation pattern of 1,2,3,4-butanetriol, tetraacetate (isomer 2). The peak fragmentation pattern is in the top panel, the compound library fragmentation match is in the bottom panel, and an overlay of the two is in the center panel.
Figure 16:
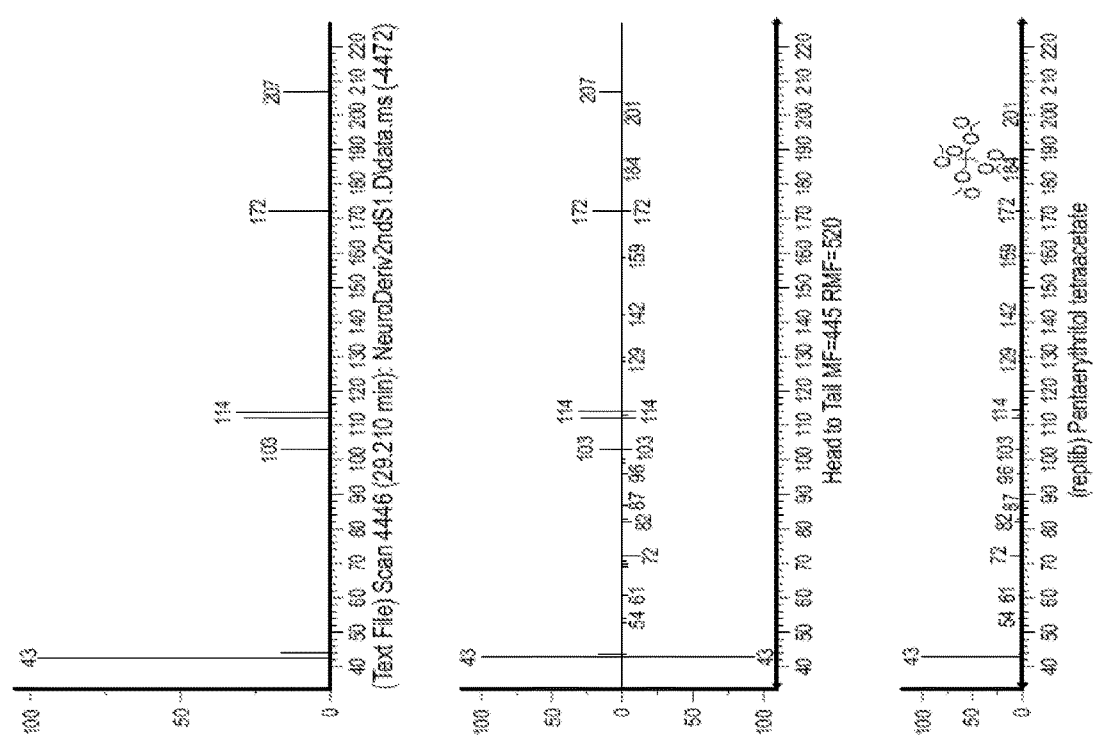
FIG. 16 is a fragmentation pattern of pentaerythritol tetraacetate. The peak fragmentation pattern is in the top panel, the compound library fragmentation match is in the bottom panel, and an overlay of the two is in the center panel.
Figure 17:
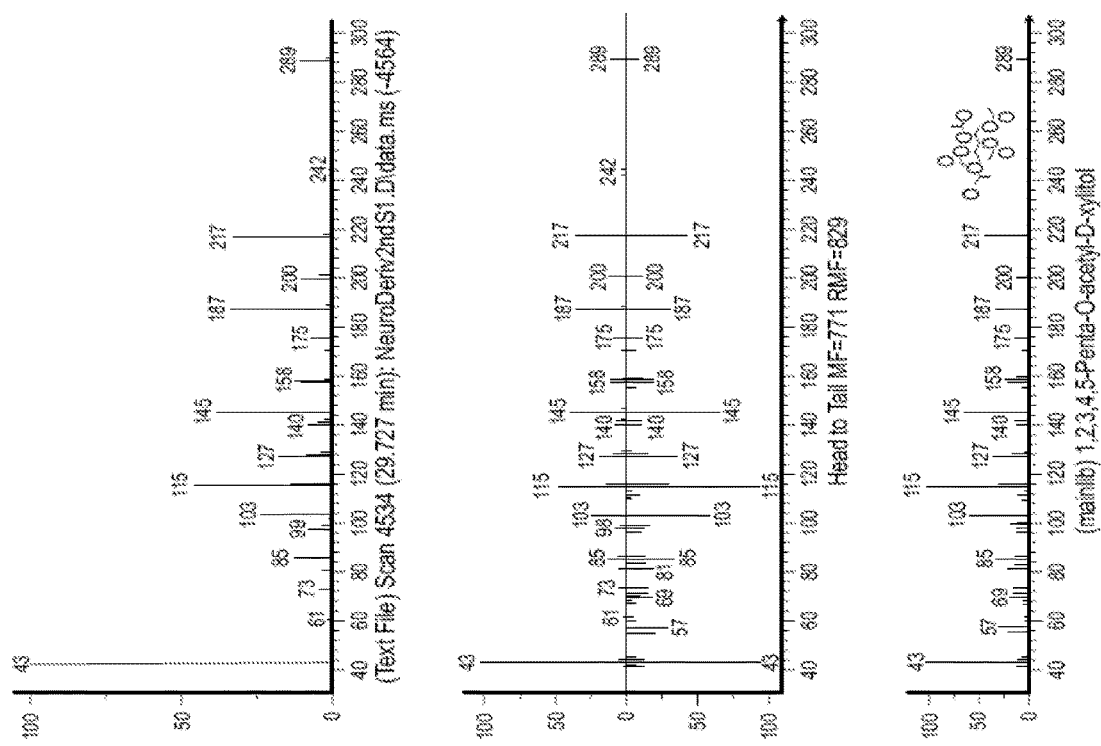
FIG. 17 is a fragmentation pattern of 1,2,3,4,5-penta-o-acetyl-D-xylitol (isomer 1). The peak fragmentation pattern is in the top panel, the compound library fragmentation match is in the bottom panel, and an overlay of the two is in the center panel.
Figure 18:
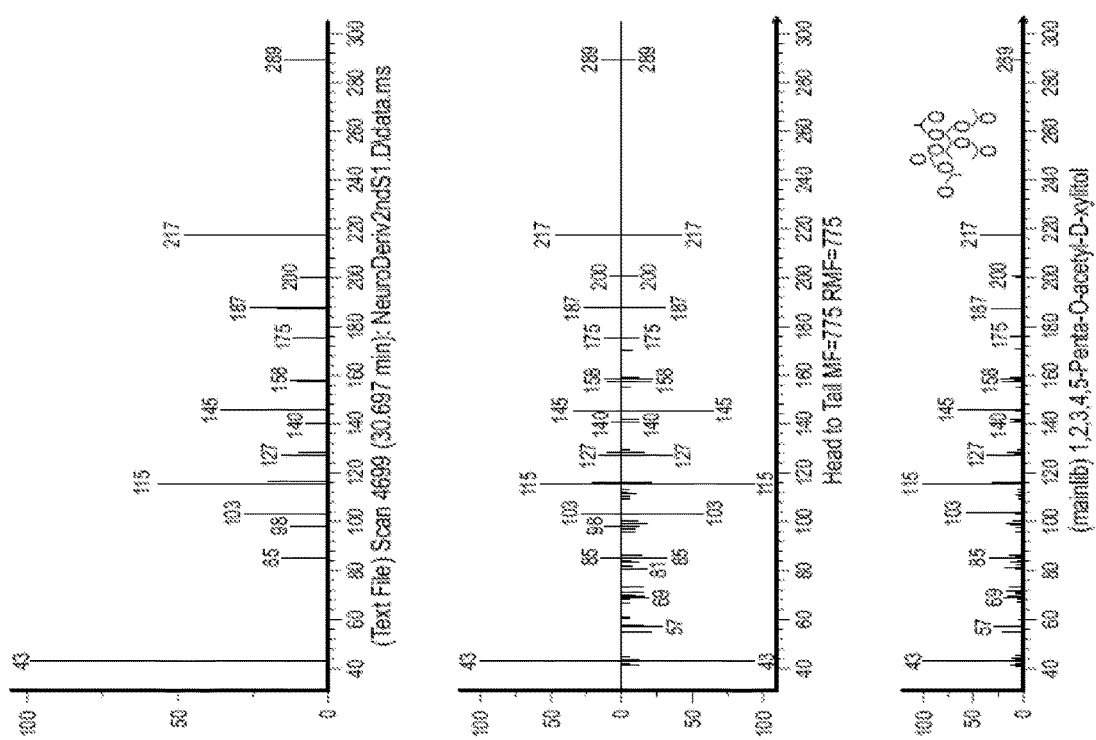
FIG. 18 is a fragmentation pattern of 1,2,3,4,5-penta-o-acetyl-D-xylitol (isomer 2). The peak fragmentation pattern is in the top panel, the compound library fragmentation match is in the bottom panel, and an overlay of the two is in the center panel.
Figure 19:
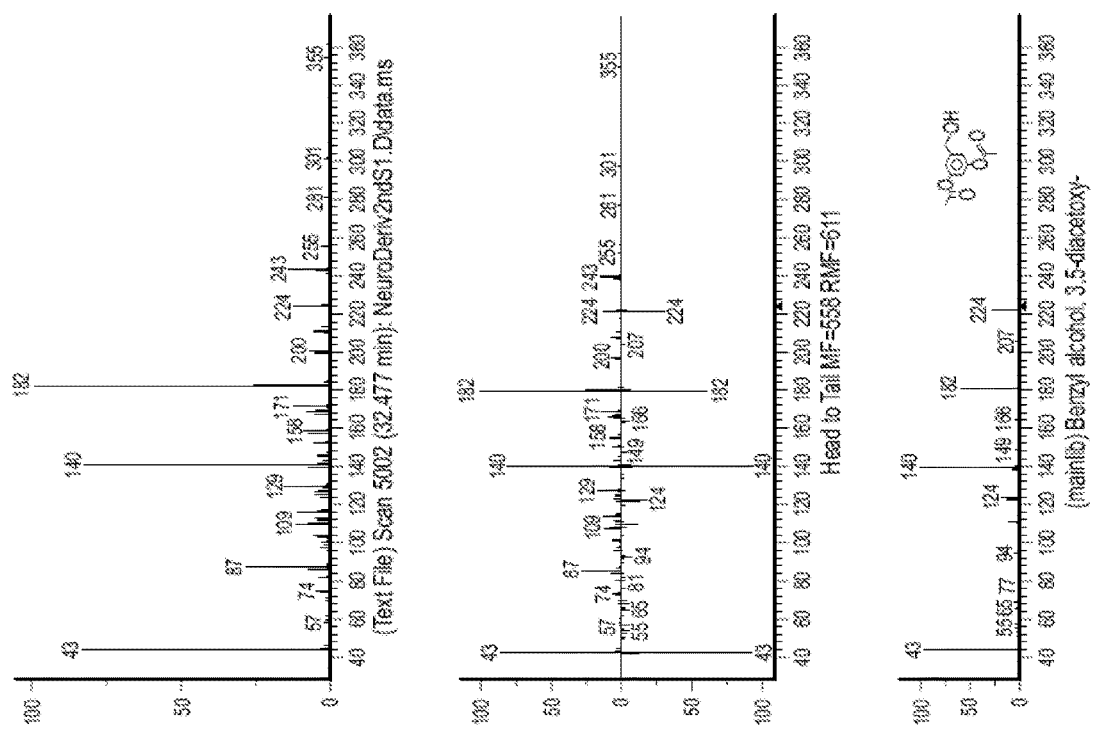
FIG. 19 is a fragmentation pattern of 3,5-diacetoxy benzyl alcohol. The peak fragmentation pattern is in the top panel, the compound library fragmentation match is in the bottom panel, and an overlay of the two is in the center panel.
Figure 20:
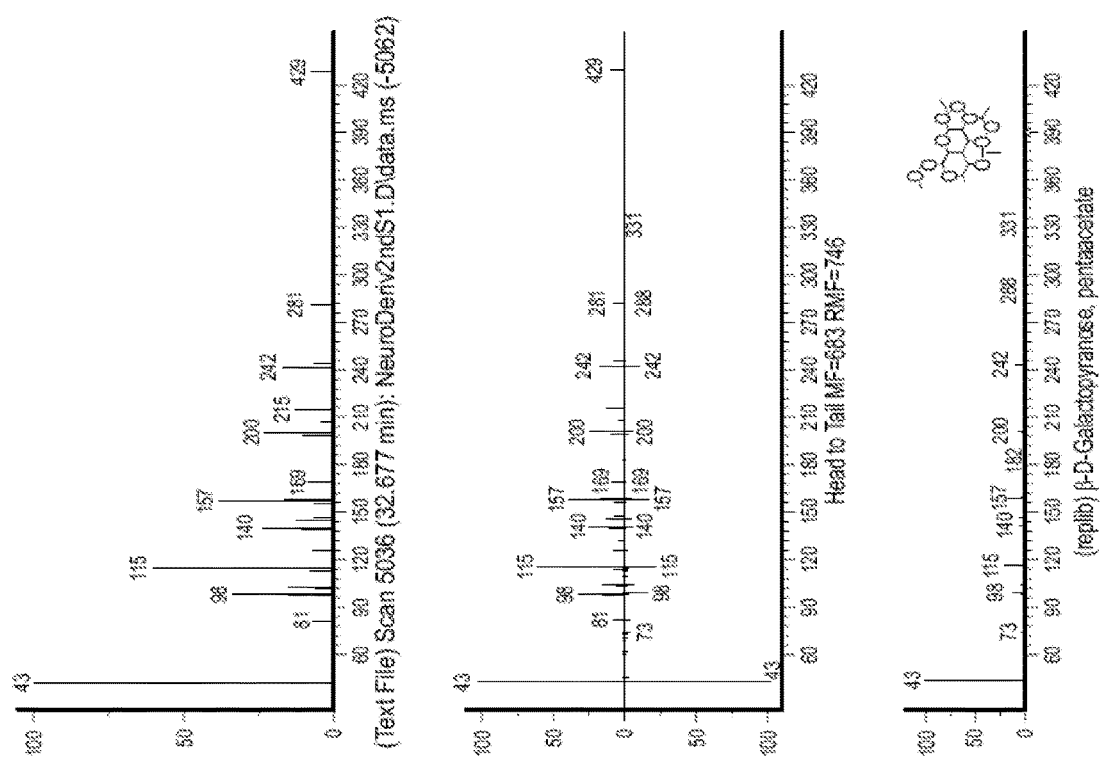
FIG. 20 is a fragmentation pattern of β-D-galactopyranose, pentaacetate. The peak fragmentation pattern is in the top panel, the compound library fragmentation match is in the bottom panel, and an overlay of the two is in the center panel.
Figure 21:
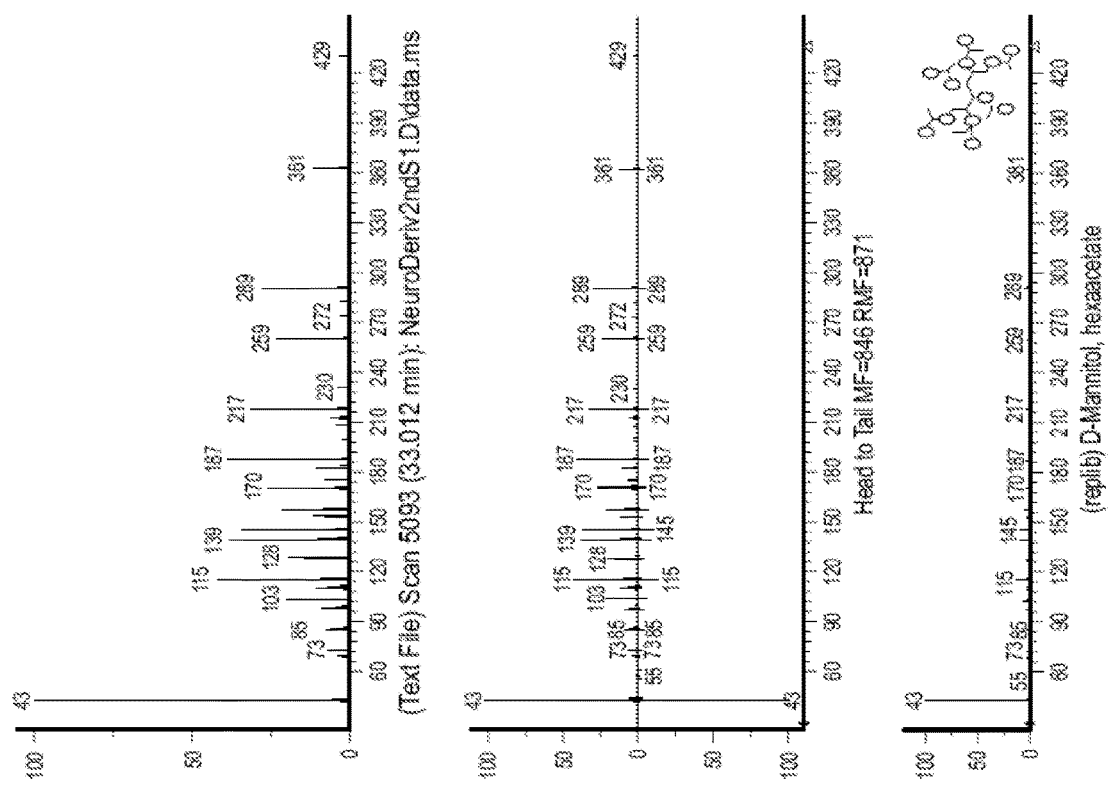
FIG. 21 is a fragmentation pattern of D-mannitol hexaacetate. The peak fragmentation pattern is in the top panel, the compound library fragmentation match is in the bottom panel, and an overlay of the two is in the center panel.
Figure 22:
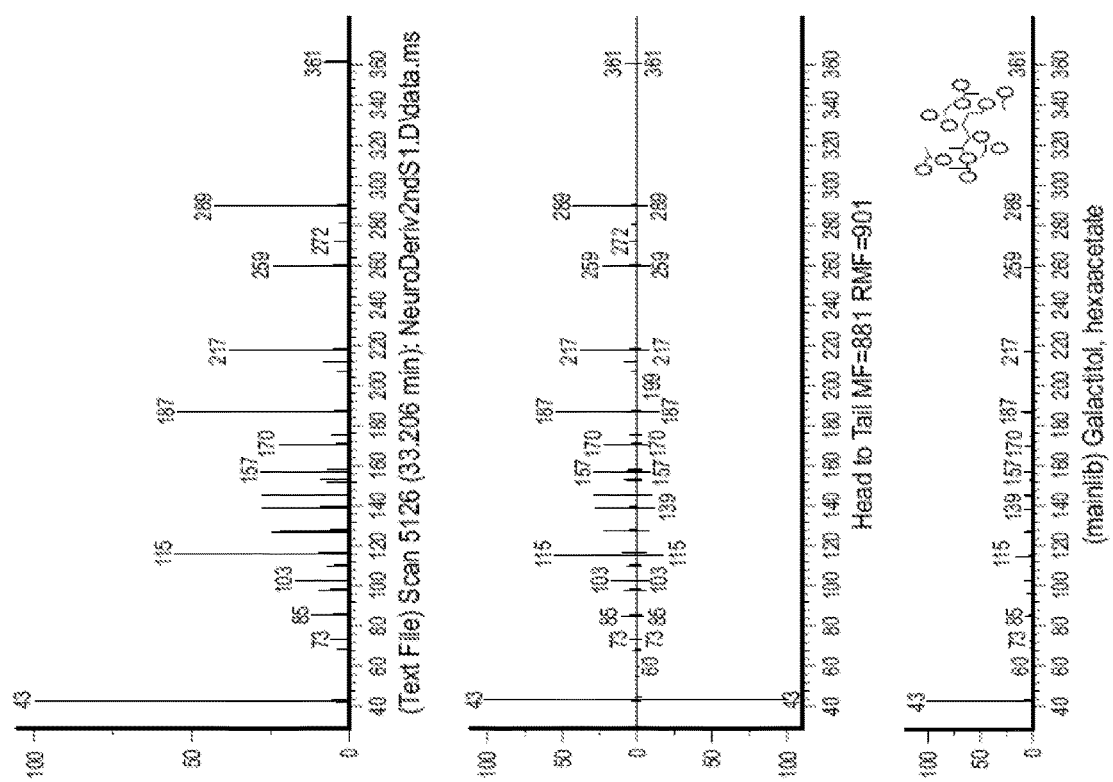
FIG. 22 is a fragmentation pattern of galacticol, hexaacetate. The peak fragmentation pattern is in the top panel, the compound library fragmentation match is in the bottom panel, and an overlay of the two is in the center panel.
Figure 23:
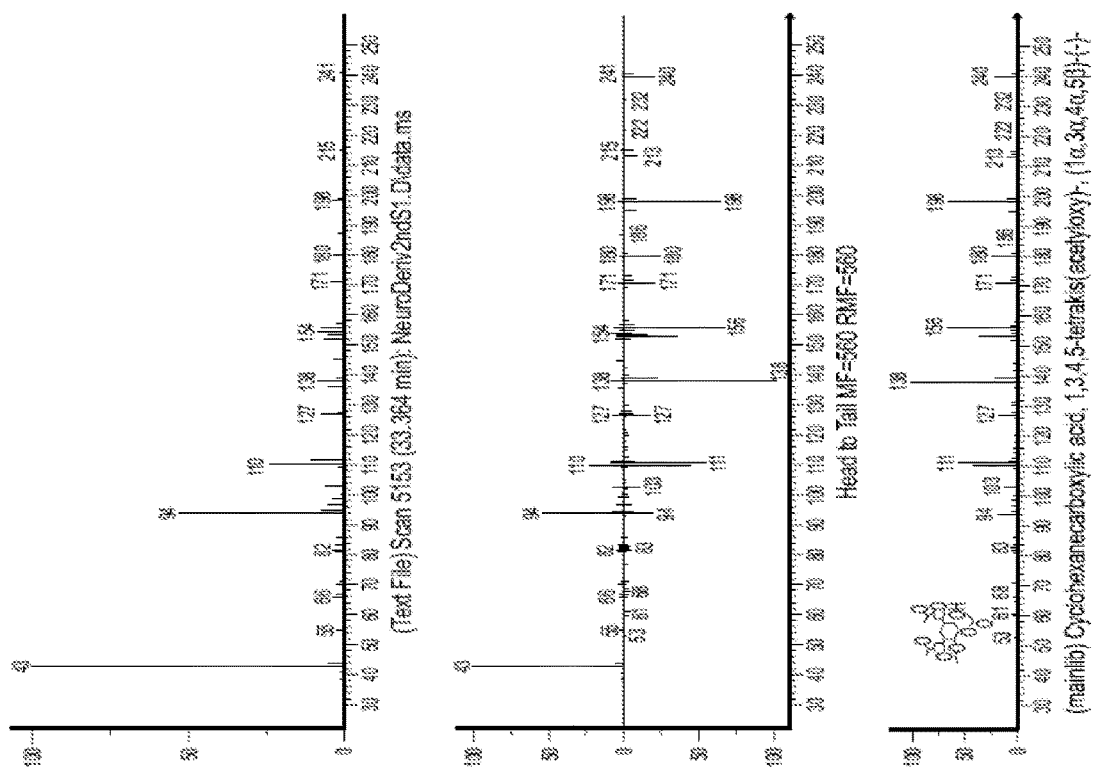
FIG. 23 is a fragmentation pattern of cyclohexane carboxylic acid, 1,2,4,5-tetrakis(acetoxy), (1α,3α,4α,5β)-(−). The peak fragmentation pattern is in the top panel, the compound library fragmentation match is in the bottom panel, and an overlay of the two is in the center panel.
Figure 24:
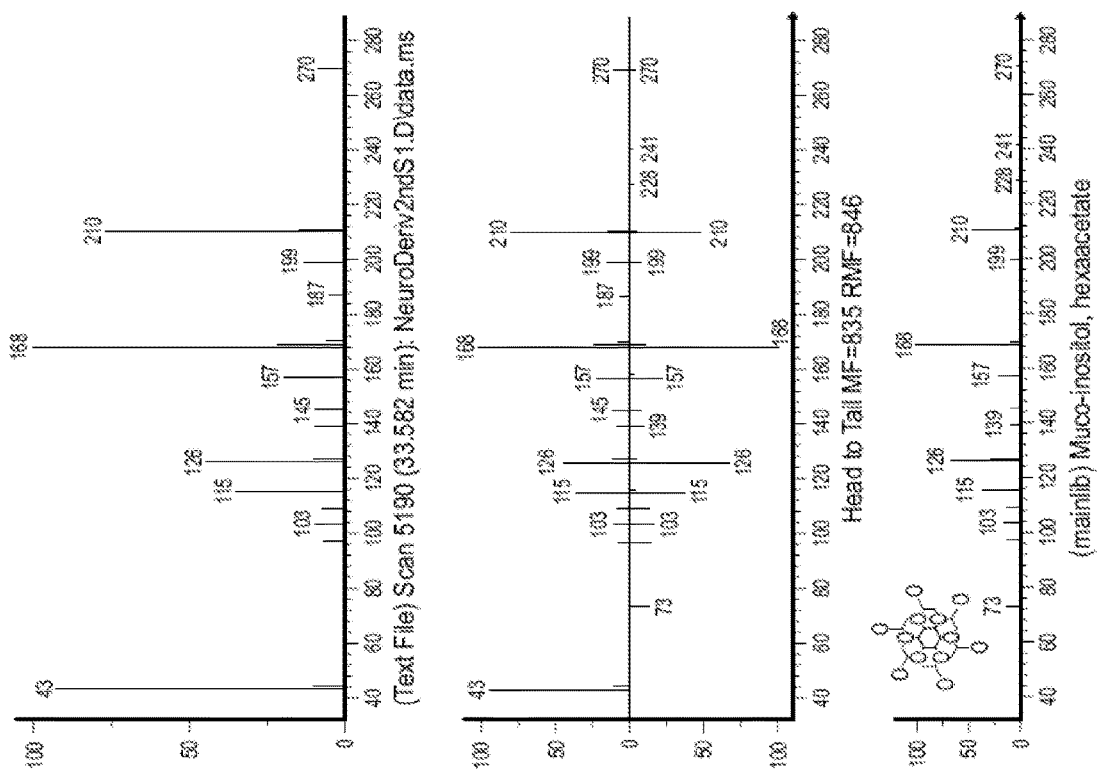
FIG. 24 is a fragmentation pattern of muco-inositol, hexaacetate. The peak fragmentation pattern is in the top panel, the compound library fragmentation match is in the bottom panel, and an overlay of the two is in the center panel.
Figure 25:
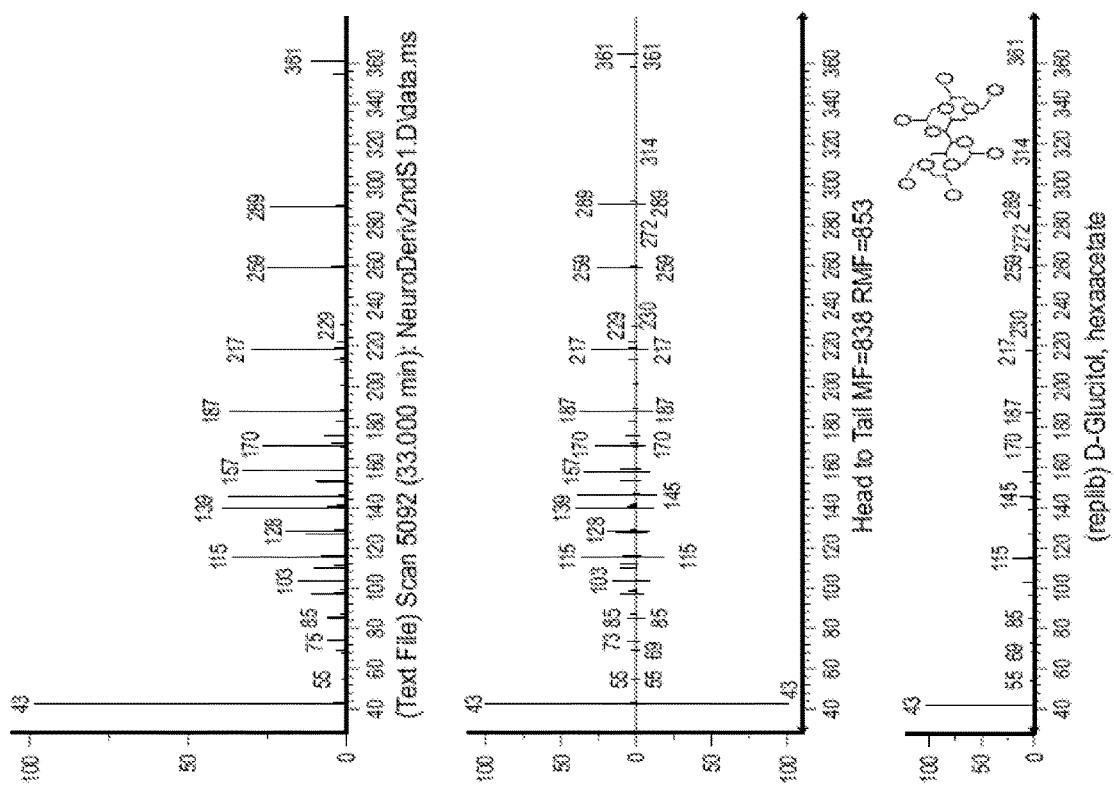
FIG. 25 is a fragmentation pattern of D-glucitol-hexaacetate. The peak fragmentation pattern is in the top panel, the compound library fragmentation match is in the bottom panel, and an overlay of the two is in the center panel.
Figure 26:
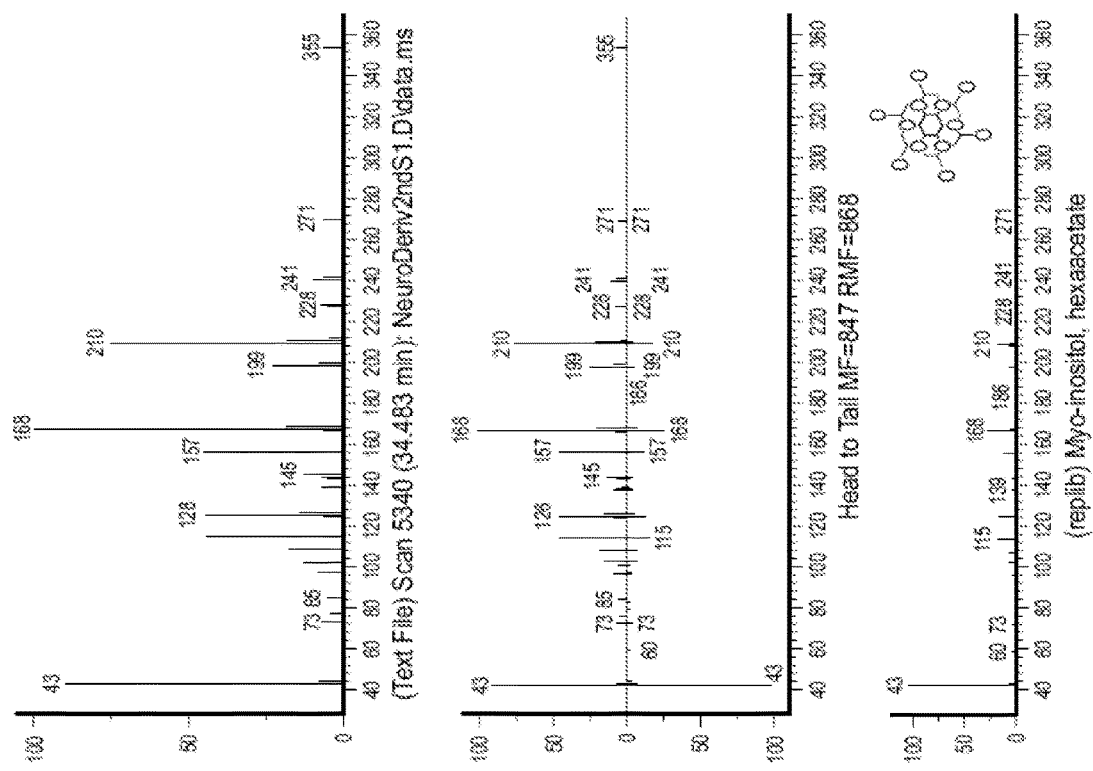
FIG. 26 is a fragmentation pattern of myo-inositol, hexaacetate. The peak fragmentation pattern is in the top panel, the compound library fragmentation match is in the bottom panel, and an overlay of the two is in the center panel.
Figure 27:
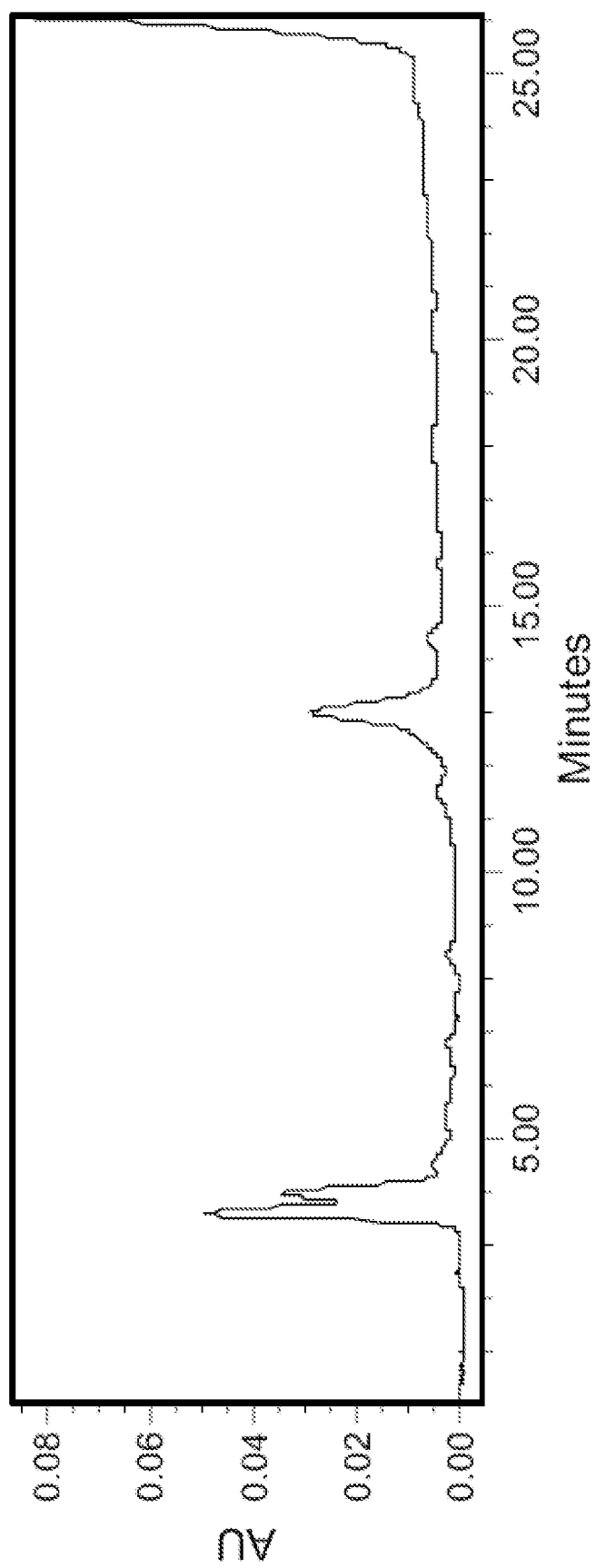
FIG. 27 is an HPLC chromatogram of a 10% ACN extract of raw Organic Yellow potato.
Figure 28:
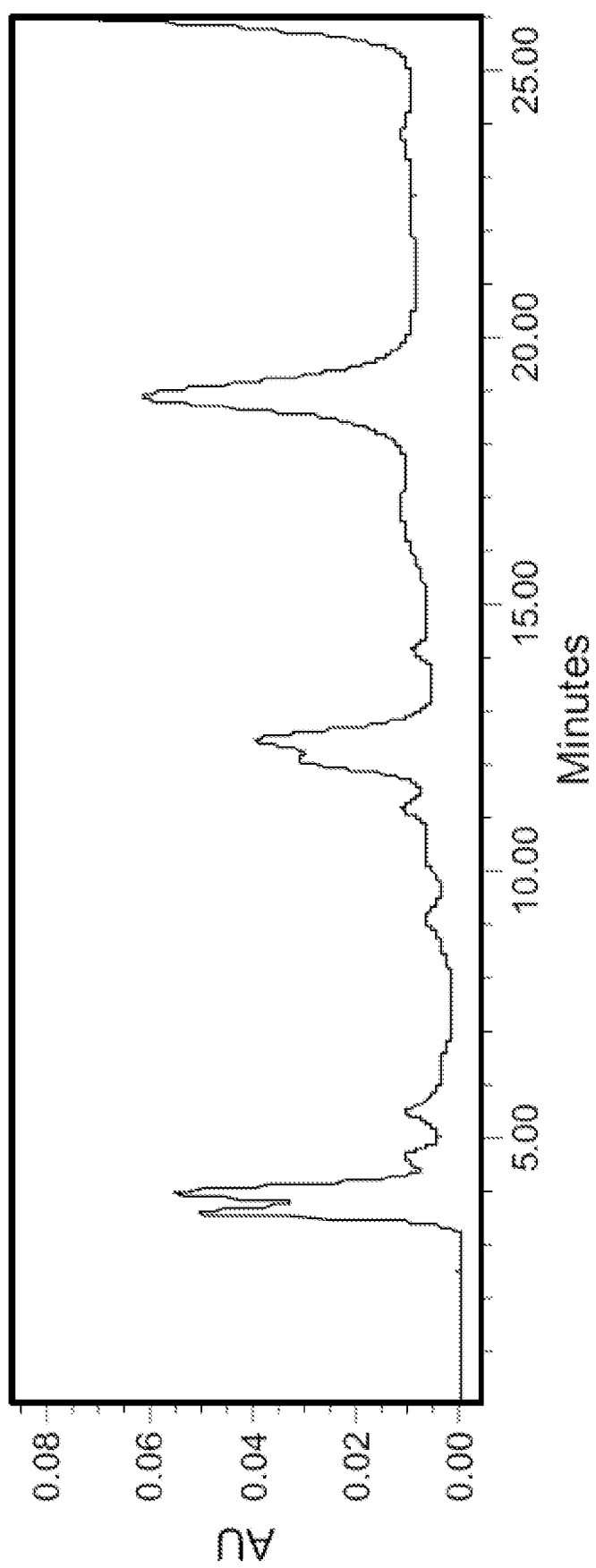
FIG. 28 is an HPLC chromatogram of a 10% ACN extract of raw Purple potato.
Figure 29:
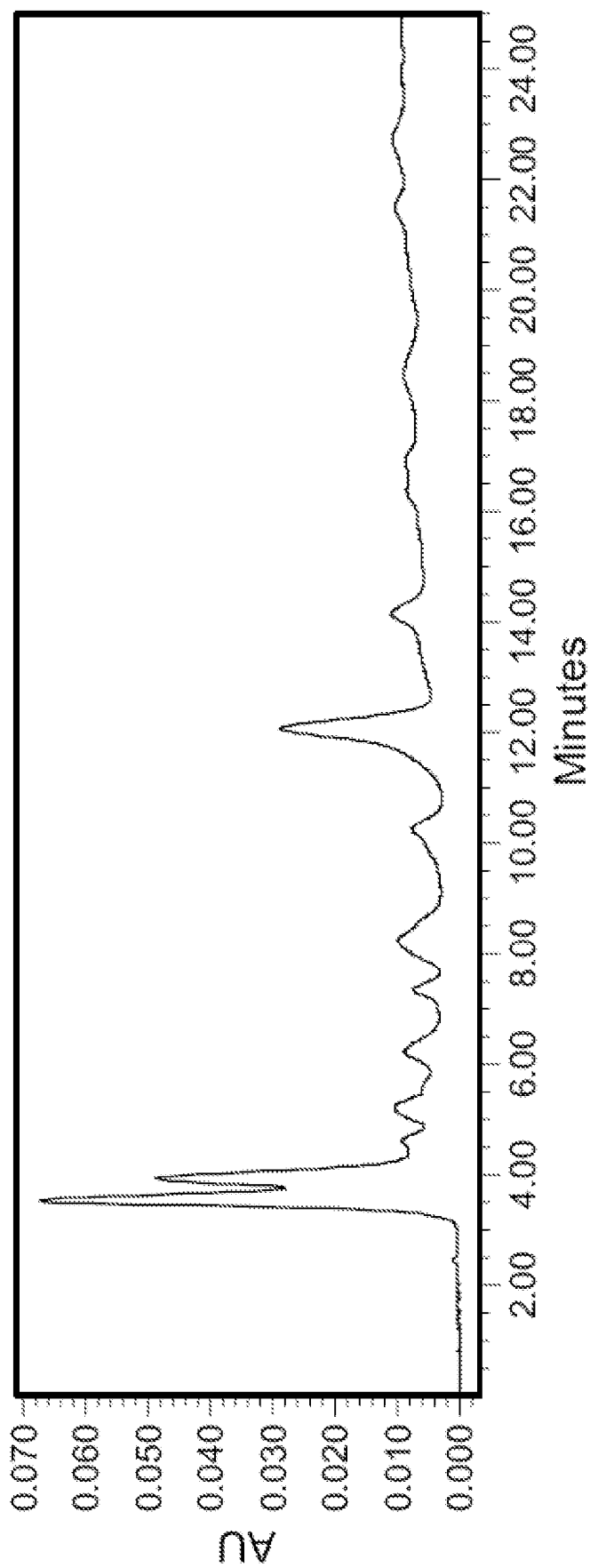
FIG. 29 is an HPLC chromatogram of a 10% ACN extract of raw Idaho Russet potato.
Figure 30:
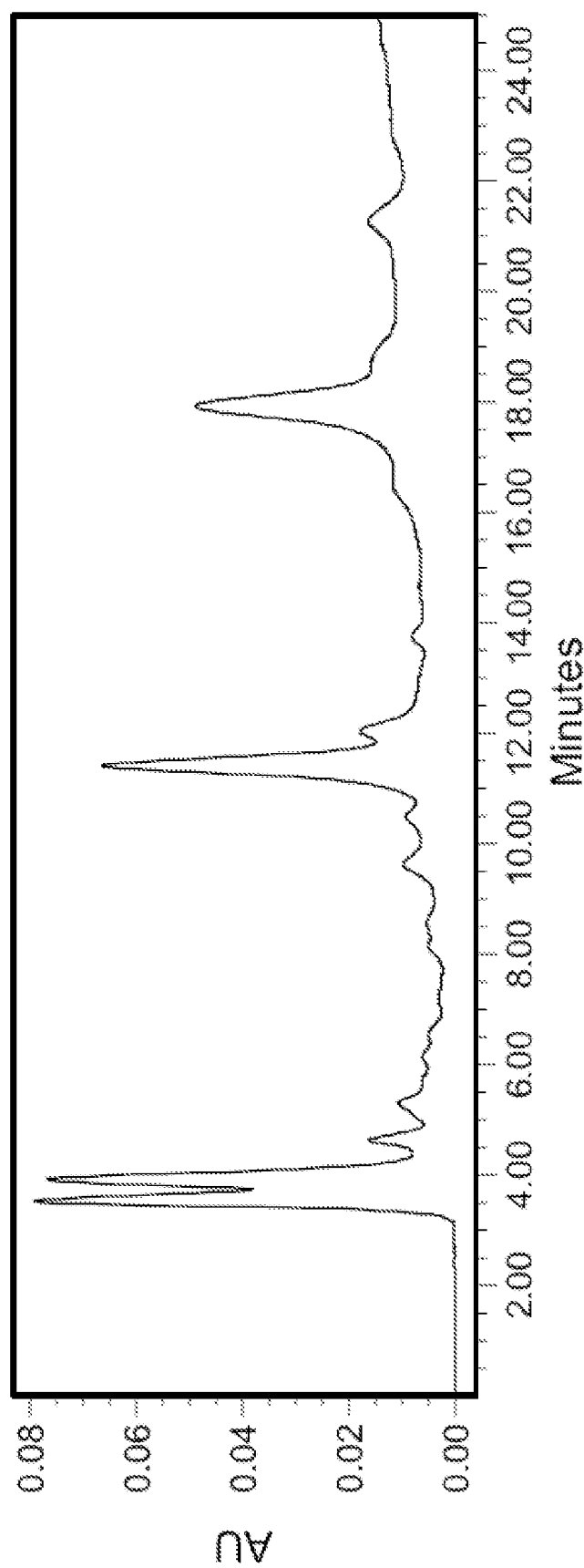
FIG. 30 is an HPLC chromatogram of a 10% ACN extract of raw Yukon Gold potato.
Figure 31:
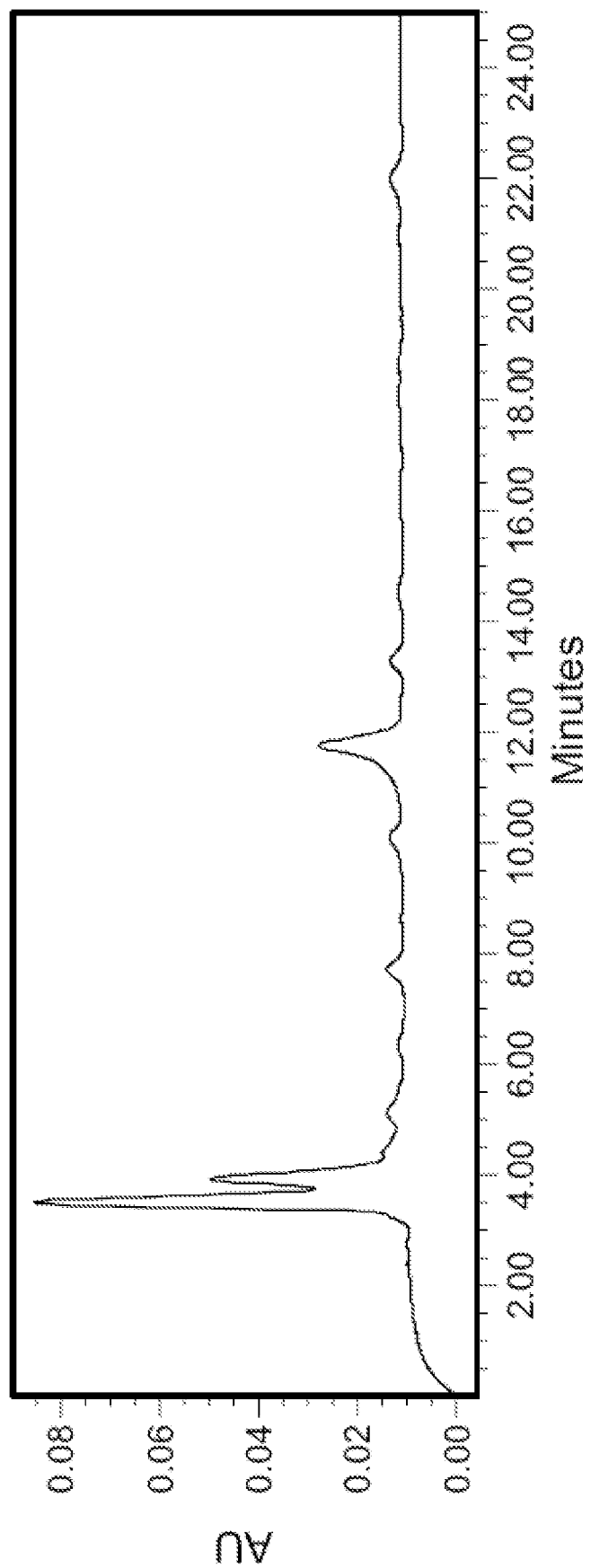
FIG. 31 is an HPLC chromatogram of a 10% ACN extract of raw sweet potato.

In some cases, a potato polysaccharide preparation can be a preparation that is obtained from potato and that contains polysaccharide material that, when derivatized and assessed using GC/MS, results in at least four major components (3,4-furan dimethanol, diacetate; 1,2,3,4,5-penta-o-acetyl-D-xylitol (isomer 1); 3,5-diacetoxy-benzyl alcohol; and D-glucitol-hexaacetate). See, e.g., Example 1. In some cases, a potato polysaccharide preparation can be a preparation that is obtained from potato and that contains polysaccharide material that, when derivatized and assessed using GC/MS, results in the compounds listed in Table 1 or results in the profile shown in FIG. 6.

In some cases, a potato polysaccharide preparation provided herein can be a substantially pure potato polysaccharide preparation. Typically, a substantially pure potato polysaccharide preparation is a preparation that contains a single peak of material (e.g., a single peak of polysaccharide material) when assessed using, for example, HPLC (see, e.g., FIGS. 2 and 32). In some cases, greater than 60, 70, 75, 80, 85, 90, 95, or 99 percent of a potato polysaccharide preparation provided herein can be polysaccharide material obtained from a potato.

Any appropriate potato species or variety can be used to obtain a potato polysaccharide preparation provided herein. For example, *Solanum tuberosum, Ipomoea batatas, S. acaule, S. bukasovii, S. leptophyes, S. megistacrolobum, S. commersonii*, or *S. infundibuliforme* can be used to obtain a potato polysaccharide preparation provided herein. In some cases, potato varieties of *S. tunerosum* such as Organic Yellow, Purple or blue varieties, Cream of the Crop, Adirondack Blue, Adirondack Red, Agata, Almond, Andes Gold, Andes Sun, Apline, Alturas, Amandine, Annabelle, Anya, Arran Victory, Atlantic, Avalanche, Bamberg, Bannock Russet, Belle de Fontenay, BF-15, Bildtstar, Bintje, Blazer Russet, Blue Congo, Bonnotte, British Queens, Cabritas, Camota, Canela Russet, Cara, Carola, Chelina, Chiloé, Cielo, Clavela Blanca, Désirée, Estima, Fianna, Fingerling, *Flava*, German Butterball, Golden Wonder, Goldrush, Home Guard, Innovator, Irish Cobbler, Jersey Royal, Kennebec, Kerr's Pink, Kestrel, Keuka Gold, King Edward, Kipfler, Lady Balfour, Langlade, Linda, Marcy, Marfona, *Maris Piper*, Marquis, Megachip, Monalisa, Nicola, Pachacoña, Pike, Pink Eye, Pink Fir Apple, Primura, Ranger Russet, Ratte, Record, Red LaSoda, Red Norland, Red Pontiac, Rooster, Russet Burbank, Russet Norkotah, Selma, Shepody, Sieglinde, Silverton Russet, Sirco, Snowden, Spunta, Up to date, Stobrawa, Superior, Vivaldi, Vitelotte, Yellow Finn, or Yukon Gold can be used to obtain a potato polysaccharide preparation provided herein.

Any appropriate method can be used to obtain a potato polysaccharide preparation provided herein. For example, raw potato material can be homogenized (e.g., homogenized with a Polytron homogenizer) in water and maintained at room temperature for a period of time (e.g., about 1 hour) with occasional shaking. The homogenate can be centrifuged (e.g., centrifuged at 4000 g for 10 minutes) to remove any larger solid material. The resulting supernatant can be loaded onto a Solid Phase Extraction cartridge (e.g., a C18 cartridge such as a Sep-Pak Plus C-18 cartridge), and the polysaccharide material eluted with 10 percent acetonitrile. Once eluted, the polysaccharide material can be dried and stored (e.g., stored at about 4° C.).

This document also provides nutritional supplement compositions containing one or more potato polysaccharide preparations provided herein. For example, a potato polysaccharide preparation provided herein obtained from Idaho Russet potatoes can be formulated into a nutritional supplement composition.

Any appropriate dose of a potato polysaccharide preparation provided herein can be used to formulate a composition provided herein (e.g., a nutritional supplement composition or potato polysaccharide preparation provided herein). For example, a potato polysaccharide preparation provided herein can be used to formulate a composition for reducing amyloid beta levels within a mammal having Alzheimer's disease. The composition can contain between about 1 mg and about 750 mg (e.g., between about 1 mg and about 500 mg, between about 1 mg and about 250 mg, between about 5 mg and about 40 mg, between about 5 mg and about 30 mg, between about 5 mg and about 20 mg, between about 6 mg and about 50 mg, between about 6 mg and about 20 mg, between about 10 mg and about 25 mg, or between about 15 mg and about 20 mg) of the potato polysaccharide component of the potato polysaccharide preparation. In some cases, a composition (e.g., a nutritional supplement composition) can be formulated to deliver about 0.05 mg of the potato polysaccharide component per kg of body weight to about 0.5 mg of the potato polysaccharide component per kg of body weight to a mammal (e.g., a human) per day. For example, a nutritional supplement composition can be formulated into a single oral composition that a human can swallow once a day to provide between about 0.05 mg of the potato polysaccharide component per kg of body weight to about 0.5 mg of the potato polysaccharide component per kg of body weight.

Any appropriate method can be used to formulate a composition provided herein (e.g., a nutritional supplement composition or potato polysaccharide preparation provided herein). For example, common formulation mixing techniques and preparation techniques can be used to make a composition (e.g., a nutritional supplement composition) having the components described herein. In addition, a composition provided herein (e.g., a nutritional supplement composition or potato polysaccharide preparation provided herein) can be in any form. For example, a composition provided herein (e.g., a nutritional supplement composition or potato polysaccharide preparation provided herein) can be formulated into a pill, capsule, tablet, gel cap, nutritional shake, nutritional bar, rectal suppository, sublingual suppository, nasal spray, inhalant, or injectable ampule. In some cases, a composition provided herein (e.g., a nutritional supplement composition) can include one or more potato polysaccharide preparations provided herein alone or in combination with other ingredients including, without limitation, gelatin, cellulose, starch, sugar, bentonite, lactic acid, mannitol, alpha lipoic acid, alpha tocopherol, L-ascorbate, or combinations thereof.

In some cases, a composition containing a potato polysaccharide preparation provided herein or a potato polysaccharide preparation provided herein can be used to increase expression of a LRP1 polypeptide, an APBB1 polypeptide, an IDE polypeptide, a GPX3 polypeptide, a GPX4 polypeptide, or a combination thereof. In some cases, a composition containing a potato polysaccharide preparation provided herein or a potato polysaccharide preparation provided herein can be used to decrease expression of an IGF1 polypeptide, a NOS2 polypeptide, or a combination thereof.

In humans, a composition containing a potato polysaccharide preparation provided herein or a potato polysaccharide preparation provided herein can be used to increase expression of a human LRP1 polypeptide, a human APBB1 polypeptide, a human IDE polypeptide, a human GPX3 polypeptide, a human GPX4 polypeptide, or a combination thereof. In some cases, a composition containing a potato polysaccharide preparation provided herein or a potato polysaccharide preparation provided herein can be used to decrease expression of a human IGF1 polypeptide, a human NOS2 polypeptide, or a combination thereof.

A human LRP1 polypeptide can have the amino acid sequence set forth in GenBank® Accession No. NP_002323.2 (GI No. 126012562) and can be encoded by the nucleic acid sequence set forth in GenBank® Accession No. NG_016444 (GI No. 284813599). A human APBB1 polypeptide can have the amino acid sequence set forth in GenBank® Accession No. O00213.2 (GI No. 12229629) and can be encoded by the nucleic acid sequence set forth in GenBank' Accession No. NG_029615.1 (GI No. 342349296). A human IDE polypeptide can have the amino acid sequence set forth in GenBank® Accession No. AAA52712.1 (GI No. 184556) and can be encoded by the nucleic acid sequence set forth in GenBank® Accession No. NG_013012.1 (GI No. 260593646). A human GPX3 polypeptide can have the amino acid sequence set forth in GenBank® Accession No. NP_002075.2 (GI No. 6006001) and can be encoded by the nucleic acid sequence set forth in GenBank® Accession No. NC_000005.10 (GI No.

568815593). A human GPX4 polypeptide can have the amino acid sequence set forth in GenBank® Accession No. AAH22071.1 (GI No. 34784795) and can be encoded by the nucleic acid sequence set forth in GenBank® Accession No. NC_000019.10 (GI No. 568815579). A human IGF1 polypeptide can have the amino acid sequence set forth in GenBank® Accession No. NP_001104753.1 (GI No. 163659899) and can be encoded by the nucleic acid sequence set forth in GenBank® Accession No. NC_000012.12 (GI No. 568815586). A human NOS2 polypeptide can have the amino acid sequence set forth in GenBank® Accession No. AAI30284.1 (GI No. 120660146) and can be encoded by the nucleic acid sequence set forth in GenBank® Accession No. NG_011470.1 (GI No. 22480926).

In some cases, a potato polysaccharide preparation provided herein or a nutritional supplement composition provided herein can be used to increase expression of polypeptides involved with the metabolism of CNS-derived amyloid beta polypeptides within the adipose tissue compartment. For example, a potato polysaccharide preparation provided herein or a nutritional supplement composition provided herein can be used to increase expression of a LRP1 polypeptide, an APBB1 polypeptide, an IDE polypeptide, a GPX3 polypeptide, or a combination thereof. In humans, a composition containing a potato polysaccharide preparation provided herein or a potato polysaccharide preparation provided herein can be used to increase expression of a human LRP1 polypeptide, a human APBB1 polypeptide, a human IDE polypeptide, a human GPX3 polypeptide, or a combination thereof, in human adipocytes.

In some cases, a potato polysaccharide preparation provided herein or a nutritional supplement composition provided herein can be used to increase expression of polypeptides involved with the metabolism of CNS-derived amyloid beta polypeptides within the white blood cell tissue compartment. For example, a potato polysaccharide preparation provided herein or a nutritional supplement composition provided herein can be used to increase expression of an APBB1 polypeptide, an IDE polypeptide, a GPX4 polypeptide, or a combination thereof. In humans, a composition containing a potato polysaccharide preparation provided herein or a potato polysaccharide preparation provided herein can be used to increase expression of a human APBB1 polypeptide, a human IDE polypeptide, a human GPX4 polypeptide, or a combination thereof, in human white blood cells.

In some cases, a potato polysaccharide preparation provided herein or a nutritional supplement composition provided herein can be used to increase or decrease expression of polypeptides involved with oxidative stress and proinflammatory pathways. For example, a composition containing a potato polysaccharide preparation provided herein or a potato polysaccharide preparation provided herein can be used to decrease expression of an IGF1 polypeptide, a NOS2 polypeptide, or a combination thereof. In humans, a composition containing a potato polysaccharide preparation provided herein or a potato polysaccharide preparation provided herein can be used to decrease expression of an IGF1 polypeptide, a NOS2 polypeptide, or a combination thereof, in human white blood cells.

The document will provide addition description in the following examples, which do not limit the scope of the invention described in the claims.

EXAMPLES

Example 1—Identification and Characterization of a Potato Polysaccharide Preparation 6 grams of a Russet potato variety of the *Solanum tuberosum* species were homogenized with a Polytron homogenizer in 20 mL water in a 50 mL centrifuge tube and kept at room temperature for 1 hour. The homogenate was centrifuged at 4000 rpm for 10 minutes. A Sep-Pak Plus C-18 cartridge was activated with 10 mL 100% acetonitrile (ACN) and washed with 10 mL 0.05% trifluoroacetic acid in water (TFA water). 10 mL of the supernatant was loaded onto the cartridge, and all $H_2O$ that passes through cartridge was collected in 1.5 mL Eppendorf tubes. Next, 10 mL of 2% ACN (in 0.05% TFA water) was passed through the column, and the elutriate was collected in 1.5 mL Eppendorf tubes. Next, 10 mL of 5% ACN (in 0.05% TFA water) was used to wash the column, and the elutriate was collected in 1.5 mL Eppendorf tubes. Finally, 10 mL of 10% ACN (in 0.05% TFA water) was collected in 1.5 mL Eppendorf tubes after passing through the column. All of the fractions were dried, and the dried fractions of the same ACN concentration were reconstituted into 1 tube in 1 mL of 0.05% TFA water for further purification via HPLC or reconstituted in 1 mL of phosphate buffered saline for use in cell treatments.

Figure 2:
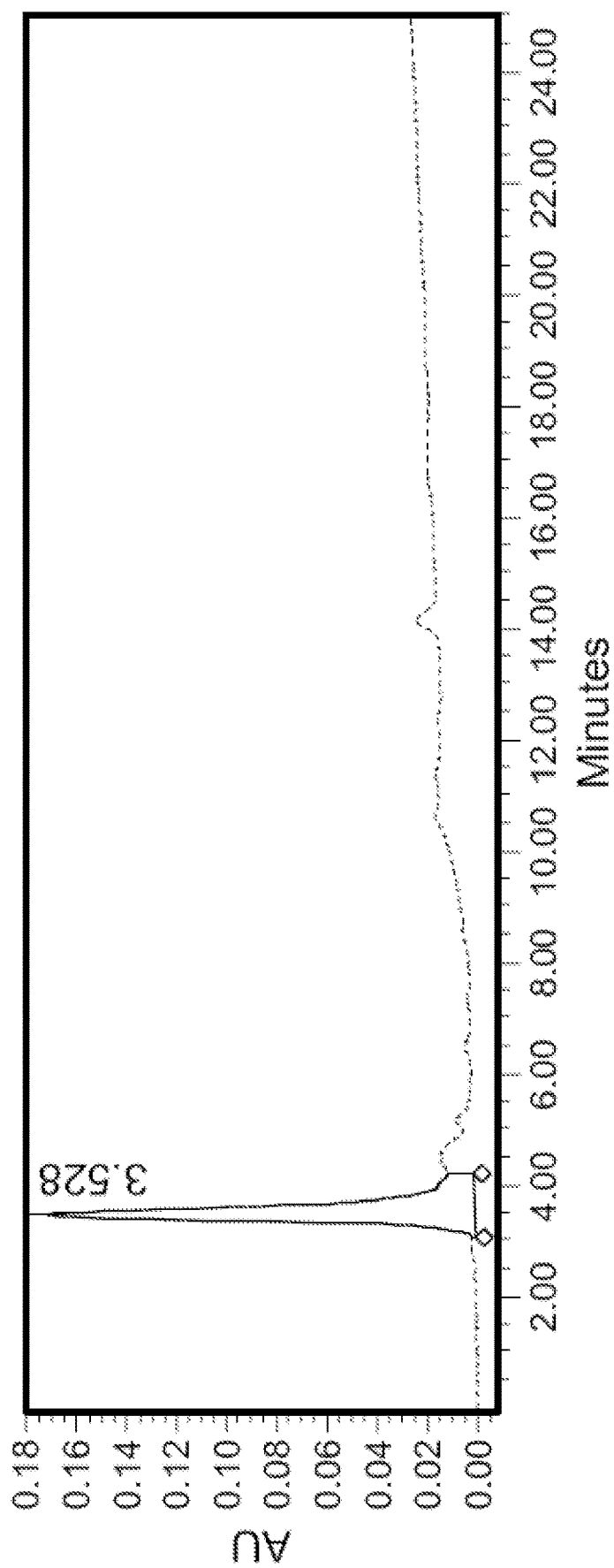
FIG. 2 is an HPLC chromatogram of collected and re-purified 3.5 minute peak material from a 10% ACN extract of raw potato shown in FIG. 1.

A Waters 2695 separations module with a photodiode array detector was used to purify the 10% ACN extract. An XterraRP C18 column (4.6×150 mm) was used for the separation with 0.05% TFA water as the mobile phase. Each HPLC run was a 20 minute gradient ranging from 0 to 2.5% ACN. The injection volume was 100 μL, and the flow rate was 0.5 mL/minute. HPLC fractionation of the 10% ACN extract yielded three major UV absorbing peaks eluted at 3.5, 3.9, and 12.1 minutes (FIG. 1). Collection and HPLC re-purification of the 3.5 minute fraction yielded a symmetrical peak displaying a maximum absorbance at 198.3 nm (FIG. 2).

Figure 3:
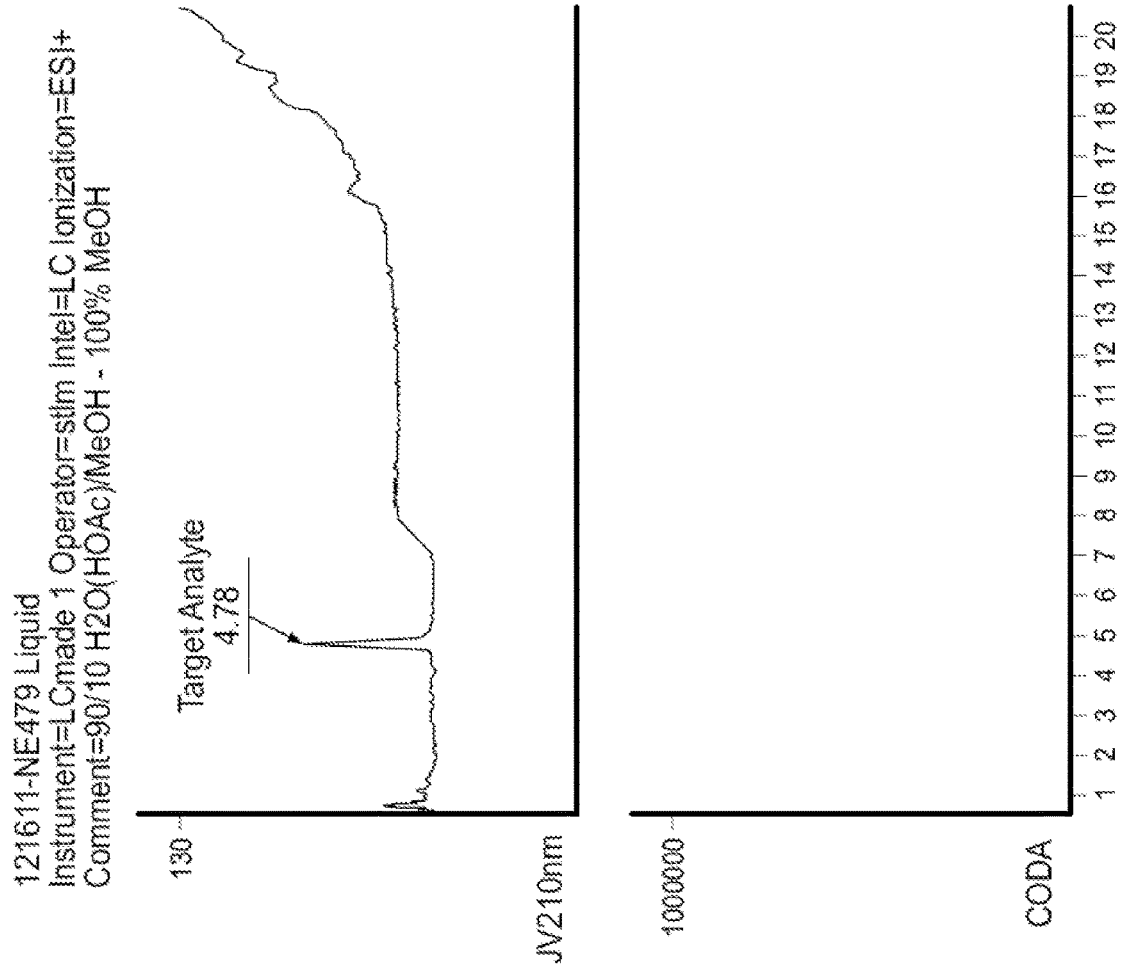
FIG. 3 is an LC/MS trace of 3.5 minute HPLC peak material.
Figure 4:
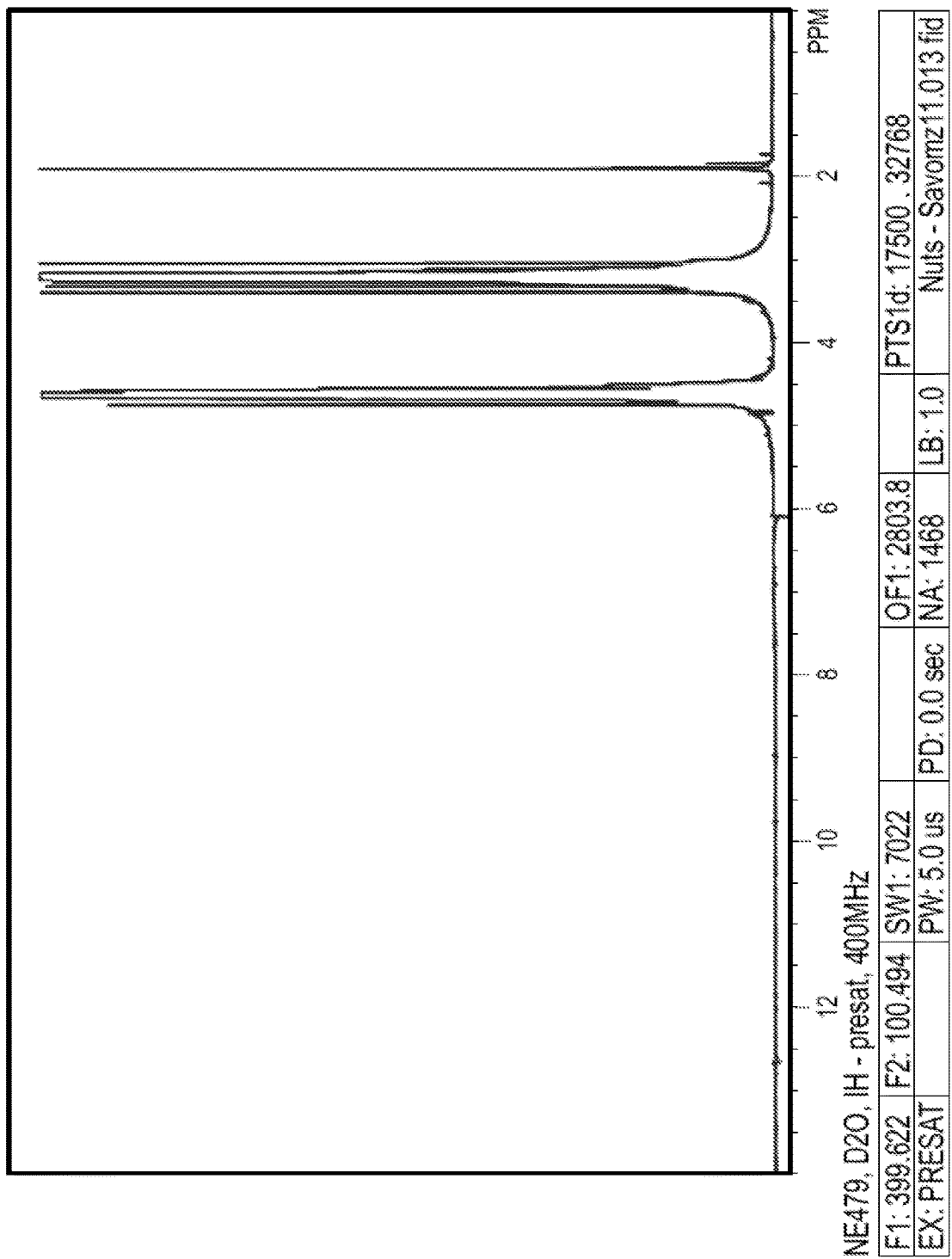
FIG. 4 is a full NMR spectrum of 3.5 minute HPLC peak material.
Figure 5:
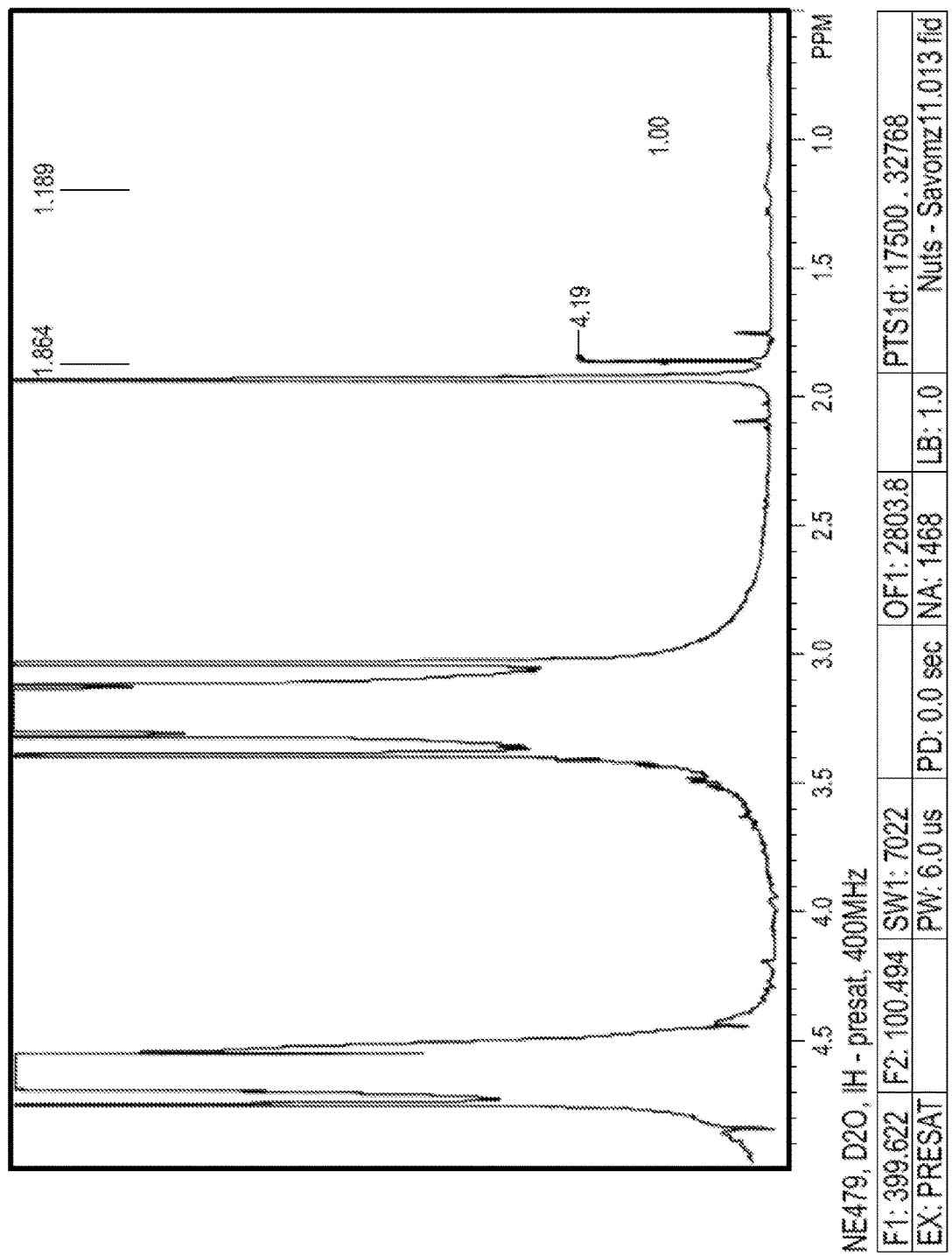
FIG. 5 is an expanded NMR spectrum of 3.5 minute HPLC peak material.

Further chemical characterization of the symmetrical 3.5 minute HPLC peak material was performed. Pooled 3.5 minute HPLC fractions were dried and reconstituted in 1 mL TFA water and subjected to tandem LC/MS/MS (FIG. 3) and NMR chemical analyses (FIGS. 4 and 5). For the NMR analysis, $^1$H-NMR was run on the sample using deuterium oxide ($D_2O$) as a solvent to further analyze the sample. The water peak at 4.65 PPM was solvent-suppressed, and the spectrum was acquired for several hours. Acetamide was detected at 3.2 PPM, along with acetonitrile at 1.9 PPM. Minor peaks were detected at 1.05 PPM, 1.17 PPM (broad peak), 1.189 PPM, and 1.864 PPM. One characteristic of polymeric materials in a proton NMR was the broadening of peaks such as the shift at 1.17 PPM. These shifts on the NMR could represent the peak at 4.8 PPM and suggested a polar, water-soluble polymer such as a polysaccharide. Taken together, these results confirmed the presence of high molecular weight polysaccharide material contained in HPLC purified fractions eluting at 3.5 minutes.

Further analysis confirmed that the HPLC purified fraction eluting at 3.5 minutes contains polysaccharide material (e.g., highly substituted complex xyloglucan material). To make the polysaccharide material analyzable by gas chromatography/mass spectroscopy (GC/MS), it was converted into its derivatized carbohydrate fragments. Briefly, the sample was concentrated to a dry residue that was hydrolyzed using trifluoroacetic acid. This was then reduced using sodium borohydride, and after borate removal, the end product was acylated using acetic anhydride and pyridine.

The end products of the reaction were injected directly on GC/MS to identify any acylated carbohydrates. Based on the end analysis, a larger carbohydrate existed in the sample. The total ion chromatogram (TIC) is shown below in FIG. 6 with appropriate peak labels below in Table 1. The major components identified are indicated in bold (peaks 3, 12, 14, and 21). The corresponding fragmentation for each compound is provided in FIGS. 7-26. For each fragmentation, the peak fragmentation pattern is on the top, the compound library fragmentation match is on the bottom, and an overlay of the two is in the center. Finally, unlabeled peaks were either column bleed or did not have a sufficient match to the compound library.

TABLE 1

Summary of GC/MS results.

| Peak | Retention Time (min) | Compound Name | Structure |
|---|---|---|---|
| 1 | 10.731 | Diacetamide | 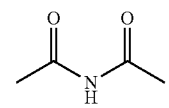 |
| 2 | 13.669 | 3-Acetoxy pyridine | 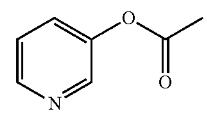 |
| 3 | 19.568 | 3,4-Furan dimethanol, diacetate | 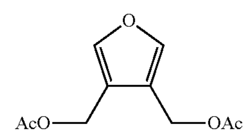 [SMILES: CC(=O)OCc1cocc1COC(C)=O] |
| 4 | 19.950 | 1,2,3-propanetriol diacetate | 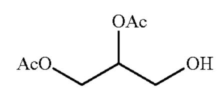 [SMILES: CC(=O)OCC(CO)OC(C)=O] |
| 5 | 23.387 | Imidazole, 2-acetamino-5-methyl | 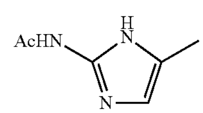 |
| 6 | 23.499 | 6,7-dihydro-5H-pyrrol[2,1-c][1,2,4]triazole-3-carboxylic acid | 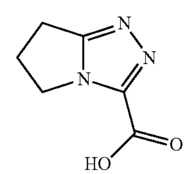 [SMILES: O=C(O)c1nnc2n1CCC2] |
| 7 | 24.304 | Acetic acid, 1-(2-methyltetrazol-5-yl) ethenyl ester | 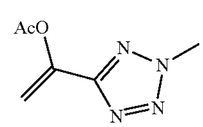 |
| 8 | 25.538 | 1,2,3,4-butanetriol, tetraacetate | 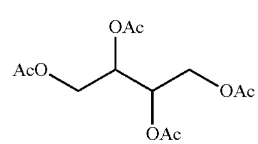 [SMILES: CC(=O)OCC(OC(C)=O)C(COC(C)=O)OC(C)=O] |
| 9 | 27.412 | (1,5)β(1,3)triacetyl D-galactosan (stereoisomer 1) | 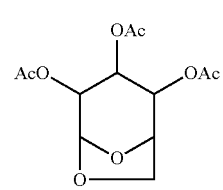 [SMILES: CC(=O)OC1C2COC(O2)C(OC(C)=O)C1OC(C)=O] |

TABLE 1-continued

Summary of GC/MS results.

| Peak | Retention Time (min) | Compound Name | Structure |
|---|---|---|---|
| 10 | 28.188 | (1,5)β(1,3)triacetyl D-galactosan (stereoisomer 2) | 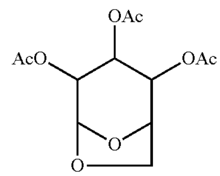 [SMILES: CC(=O)OC1C2COC(O2)C(OC(C)=O)C1OC(C)=O] |
| 11 | 29.210 | Pentaerythritol tetraacetate | 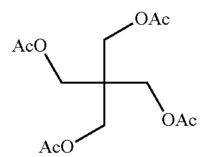 [SMILES: CC(=O)OCC(COC(C)=O)(COC(C)=O)COC(C)=O] |
| 12 | 29.727 | 1,2,3,4,5-penta-o-acetyl-D-xylitol (isomer 1) | 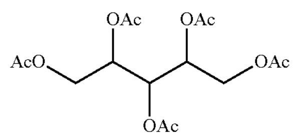 [SMILES: CC(=O)OCC(OC(C)=O)C(OC(C)=O)C(COC(C)=O)OC(C)=O] |
| 13 | 30.697 | 1,2,345-penta-o-acetyl-D-xylitol (isomer 2) | 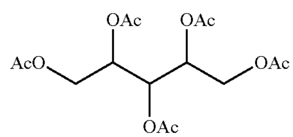 [SMILES: CC(=O)OCC(OC(C)=O)C(OC(C)=O)C(COC(C)=O)OC(C)=O] |
| 14 | 32.477 | 3,5-diacetoxy-benzyl alcohol | 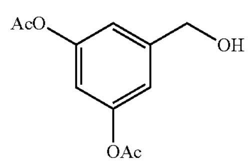 [SMILES: CC(=O)Oc1cc(CO)cc(OC(C)=O)c1] |
| 15 | 32.677 | β-D-glucopyranose, pentaacetate | 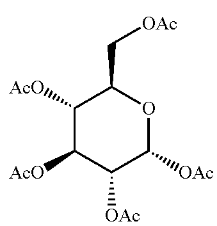 [SMILES: CC(=O)OC[C@H]1O[C@H](OC(C)=O)[C@H](OC(C)=O)[C@@H](OC(C)=O)[C@@H]1OC(C)=O] |
| 16 | 33.012 | D-mannitol hexaacetate | 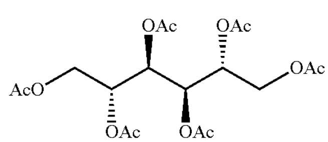 [SMILES: CC(=O)OC[C@@H](OC(C)=O)[C@@H](OC(C)=O)[C@H](OC(C)=O)[C@@H](COC(C)=O)OC(C)=O] |
| 17 | 33.106 | β-D-galactopyranose, pentaacetate | 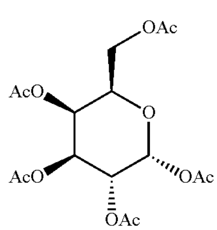 [SMILES: CC(=O)OC[C@H]1O[C@H](OC(C)=O)[C@H](OC(C)=O)[C@@H](OC(C)=O)[C@H]1OC(C)=O] |

TABLE 1-continued

Summary of GC/MS results.

| Peak | Retention Time (min) | Compound Name | Structure |
|---|---|---|---|
| 18 | 33.206 | Galacticol, hexaacetate | 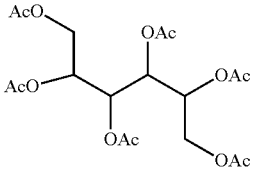 [SMILES: CC(=O)OCC(OC(C)=O)C(OC(C)=O)C(OC(C)=O)C(COC(C)=O)OC(C)=O] |
| 19 | 33.364 | Cyclohexane carboxylic acid, 1,2,45-tetrakis(acetoxy), (1α,3α,4α,5β)-(-) | 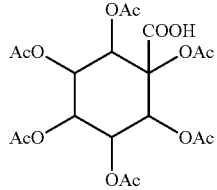 [SMILES: CC(=O)OC1C(OC(C)=O)C(OC(C)=O)C(OC(C)=O)(C(=O)O)C(OC(C)=O)C1OC(C)=O] |
| 20 | 33.582 | Muco-inositol, hexaacetate | 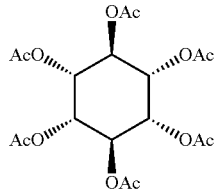 [SMILES: CC(=O)O[C@H]1[C@H](OC(C)=O)[C@@H](OC(C)=O)[C@@H](OC(C)=O)[C@H](OC(C)=O)[C@H]1OC(C)=O] |
| 21 | 33.006 | D-glucitol-hexaacetate | 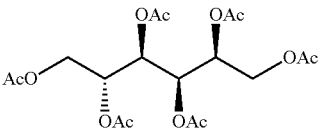 [SMILES: CC(=O)OC[C@H](OC(C)=O)[C@@H](OC(C)=O)[C@H](OC(C)=O)[C@@H](COC(C)=O)OC(C)=O] |
| 22 | 34.463 | Myo-inositol, hexaacetate | 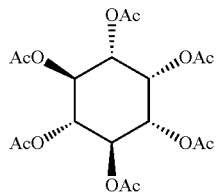 [SMILES: CC(=O)O[C@H]1[C@H](OC(C)=O)[C@@H](OC(C)=O)[C@H](OC(C)=O)[C@@H](OC(C)=O)[C@H]1OC(C)=O] |

These results demonstrate the presence of sugar monomers that serve as building blocks for a larger carbohydrate. It appeared from these multiple lines of analysis that the potato polysaccharide preparation is a highly substituted complex xyloglucan.

Example 2—Sweet Potatoes and Multiple Varieties of Potatoes Exhibit the Presence of Potato Polysaccharide Material Six grams of potato material from multiple varieties of *Solanum tuberosum* (Organic yellow, Purple, Idaho Russet, and Yukon Gold) and six grams of material from sweet potatoes (*Ipomoea batatas*) were extracted in 20 mL of water. 10 mL of that water was then loaded onto a sep-pak cartridge, and the cartridge was then eluted with 10 mL of 10% ACN. The ACN was then dried, and the residue was dissolved in 1 mL of water. A 100 µL injection of this water was assessed using HPLC.

The HPLC chromatograms demonstrated that the amount of the first peak (at 3.5 minutes at 210 nm) was the same for all five types of potatoes tested (FIGS. 27-31).

Figure 32:
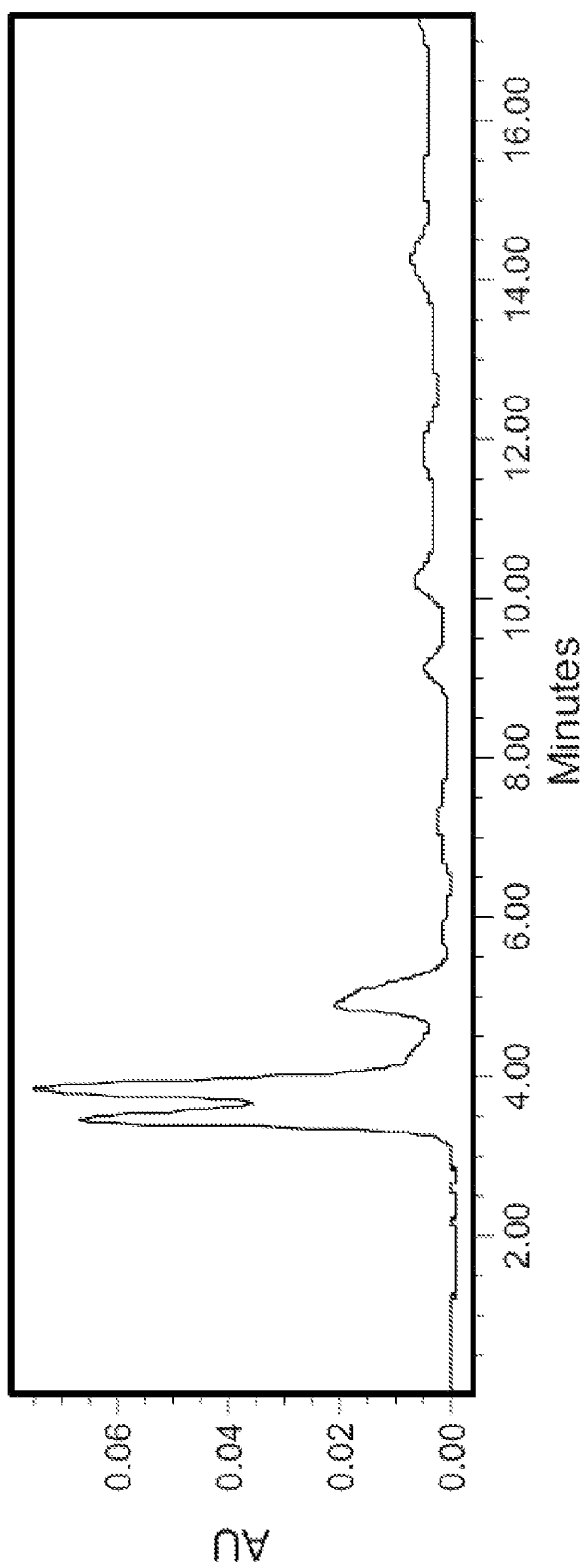
FIG. 32 is an HPLC chromatogram of a 10% ACN extract of boiled Purple potato.

In another experiment, material was extracted from a boiled Purple potato and analyzed. The peak at 3.5 minutes was not reduced in the boiled potato (FIG. 32).

Figure 33:
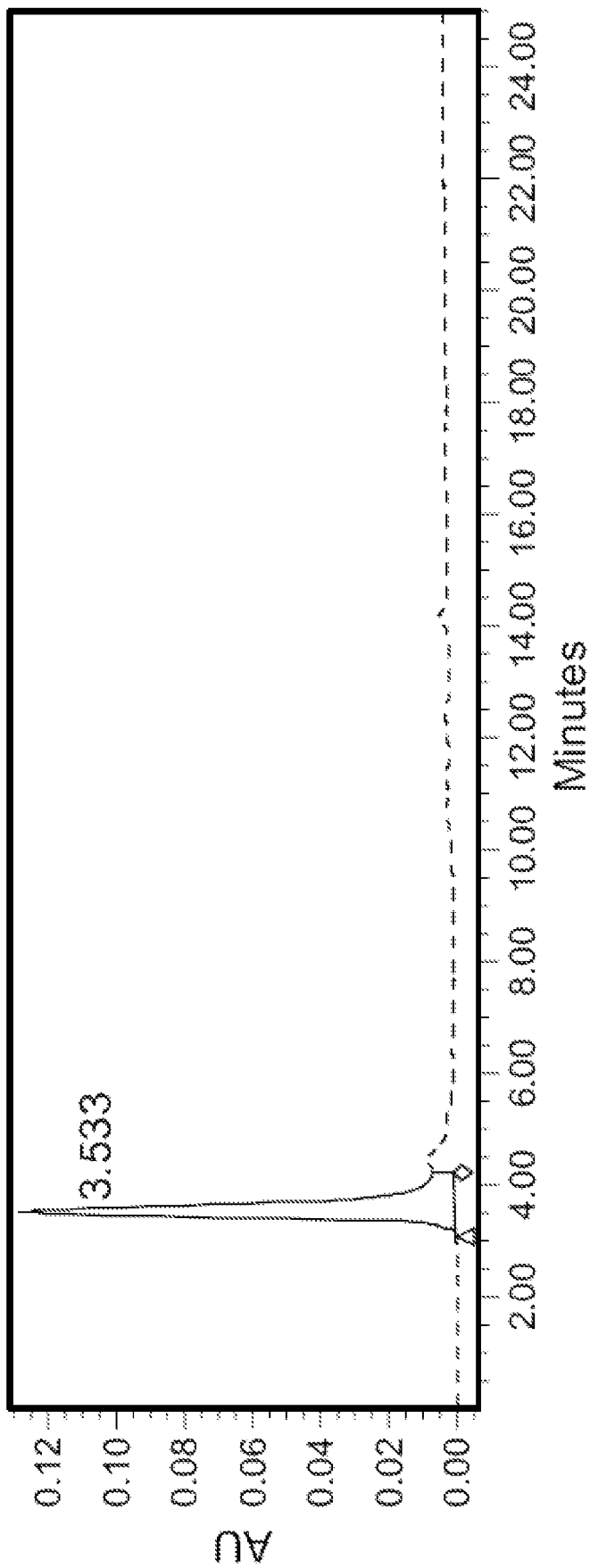
FIG. 33 is an HPLC chromatogram of two pooled fraction collections from Idaho Russet potatoes.

The 3.5 minute peak from two pooled fraction collections from Idaho Russet potatoes was collected, dried, and reconstituted in 100 µL of water. The material was then injected into the HPLC yielding a single peak at 3.5 minutes (FIG. 33). Taken together, these results demonstrate that potatoes within the *Solanum tuberosum* and *Ipomoea batatas* species contain potato polysaccharide material.

Example 3—Analysis of a Potato Polysaccharide Preparation

Figure 34:
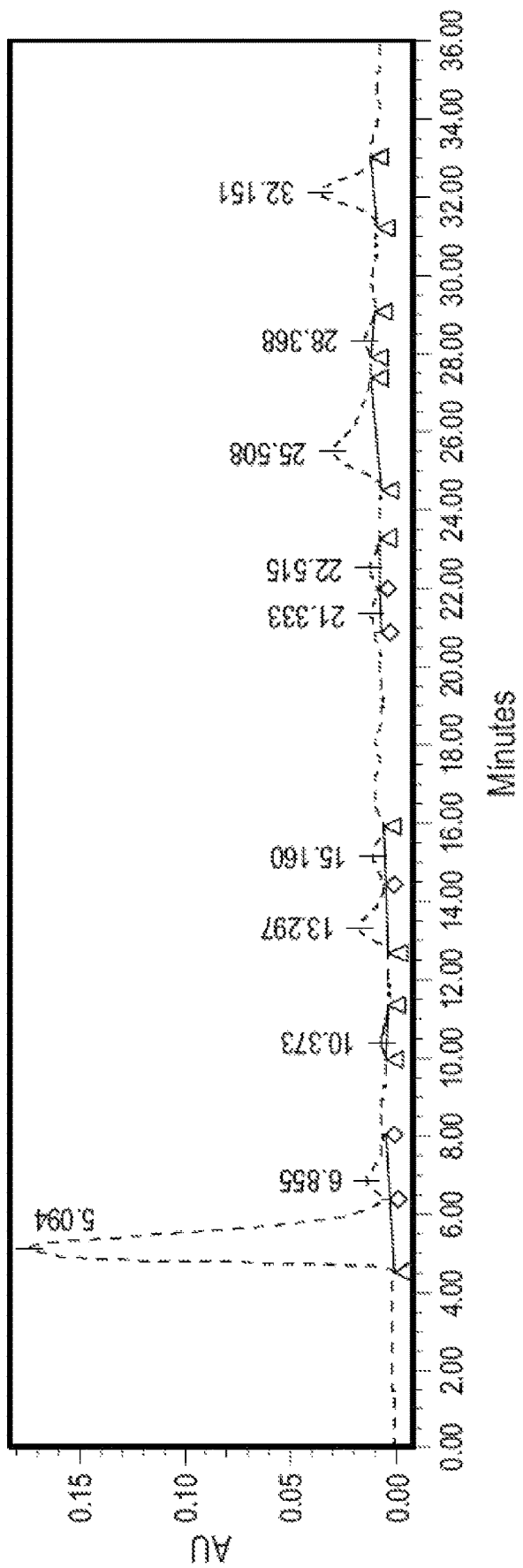
FIG. 34 is an HPLC chromatogram of fractions collections from 3 g of purple potatoes.

A potato polysaccharide preparation was purified using HPLC from 3 g of purple potato. The potato polysaccharide peak was eluted at about 5 minutes (FIG. 34). This peak was obtained using a different chromatographic column (10 mm×150 mm) as compared to the column used to obtain the 3.5 minute peak. Since the column was a larger preparative column and the flow rate was 1.5 mL/minute, the elution time of the potato polysaccharide was 5 minutes.

Example 4—Use of Potato Polysaccharide Preparations to Reduce Amyloid Beta Levels in Zucker Diabetic Fatty Rats To assess the ability of potato polysaccharide preparations to reduce amyloid beta levels within a mammal having Alzheimer's disease, blood, the livers, and abdominal fat from rats of four groups of experimental animals were collected, weighed, and examined as described in this Example.

Extraction and Purification of a Potato Polysaccharide Preparation

Typically, 6 g of potato were homogenized with a Polytron homogenizer in 20 mL water in a 50 mL centrifuge tube and kept at room temperature for 1 hour. The homogenate was centrifuged at 4000 rpm for 10 minutes and the supernatant fraction was reserved. 10 mL of the supernatant fraction was percolated through a Sep-Pak Plus C-18 cartridge previously activated with 10 mL 100% acetonitrile (ACN) followed by 10 mL 0.05% trifluoroacetic acid in water (TFA water). Following successive low ACN washes, semi-purified potato polysaccharide preparation was eluted in 10 mL 10% ACN in 0.05% TFA water. The eluent fraction was dried and reconstituted in 1 mL 0.05% TFA water for further purification via HPLC.

The reconstituted 10% ACN eluent fraction was subjected to HPLC purification utilizing a Waters Xterra RP C18 column (4.6×150 mm) and Waters 2695 separations module with a photodiode array detector. HPLC purification employed a shallow 20 minute gradient ranging from 0 to 2.5% in 0.05% TFA water at a flow rate of 0.5 mL/min. Collection and HPLC re-purification of a major 198 nm UV absorbing peak at 3.5 minutes yielded a symmetrical HPLC peak containing highly purified potato polysaccharide preparation. The purified HPLC fraction was dried and reconstituted in phosphate buffered saline (PBS) for use in biological experiments.

Potato Polysaccharide Preparation Formulation

Purified potato polysaccharide preparation (10 mL stock solution at 5 mg/mL concentration) was stored at 4° C. The vehicle for the study was sterile water (Catalog number 002488, Butler Schein). Each week, the stock solution was diluted 1:100 in sterile water (0.05 mg/mL) and dispensed into daily aliquots. All vehicle and drug solutions were stored at 4° C. and administered at room temperature daily by oral gavage (PO) in a volume of 1 mL/animal (0.15 mg/kg dose based on estimated body weight of 350 g).

In Vivo Animal Model

The Zucker Diabetic Fatty (ZDF) rat model was used (Carley and Severson, *Biochim. Biophys. Acta*, 1734:112-26 (2005)).

Experimental Animals

Twenty-two 7-week old, male Zucker Diabetic Fatty rats (ZDF, Code: 370) and twenty-two 7-8 week old, male ZDF Lean rats (Code: 371) were purchased from Charles Rivers Laboratories (Wilmington, Mass.). The study animals were allowed an acclimation period of 4 days prior to baseline blood collections, at which time two extra animals from each strain were dropped from the study based on baseline body weight. The rats were housed two per cage and maintained in the Innovive caging system (San Diego, Calif.) upon arrival at PhysioGenix, Inc. Cages were monitored daily to ensure the Innovive system maintained 80 air changes per hour and positive pressure. In accordance with the Guide for Care and Use of Laboratory Animals (Eighth Edition), rat rooms were maintained at temperatures of 66-75 degrees Fahrenheit and relative humidity between 30% and 70%. The rooms were lit by artificial light for 12 hours each day (7:00 AM-7:00 PM). Animals had free access to water and Purina 5008 rodent food (Waldschimdt's, Madison, Wis.) for the duration of the study except during fasted experiments.

Dosing and Grouping

Two types of rats were used for the study: homozygous obese ZDF/ZDF and heterozygous lean littermates. The rats within the groups were then chosen at random and divided into groups of 10. Group 1 was the homozygous ZDF/ZDF vehicle fed rats, group 2 was the homozygous ZDF/ZDF potato polysaccharide preparation fed, group 3 was the lean vehicle fed rat and group 4 was the lean potato polysaccharide preparation fed rats. The vehicle was distilled water and the potato polysaccharide preparation was given daily each morning via oral gavage at a dosage of 0.05 mg per animal. The dose was usually given in 1 mL of water. Rats were caged in groups and maintained in 12 hours light/12 hours dark (7 am-7 pm). The study lasted for 28 days and all animals were euthanized by isoflurane overdose and thoracotomy following the collection of fasted blood glucose data on Day 28 of the Study. Blood was collected via descending vena cava. Liver and abdominal fat were collected, weighed, and a portion of the left lateral liver lobe and abdominal fat were placed into individual histology cassettes and snap frozen in liquid nitrogen. General pathological observations were recorded.

RNA Isolation

Total RNA extracted from rat tissue samples was isolated and purified using the RNeasy mini kit (Qiagen, Valencia, Calif.). Typically, 100 mg of tissue was resuspended in 1.8 mL of RLT lysis buffer (Qiagen) and homogenized with a polytron homogenizer for 30 seconds. Blood RNA was isolated using the PAX RNA kit (Qiagen).

DNA Microarray Analyses

DNA microarray analyses were performed using a system provided by Agilent. Arrays included four arrays per chip (Agilent 4×44K chip). Total RNA was reverse transcribed (1000 ng) using T7 primers and labeled and transcribed using Cyanine-3 dye. Each array was hybridized with at least 1.65 µg of labeled cRNA at 65° C. for 18 hours. Arrays were scanned using an Agilent array scanner. The microarray platform can determine a minimum of a 15% change in gene expression.

Real-Time PCR Analyses

Real-time PCR analysis of gene expression was performed to validate the DNA microarray data sets. GAPDH was used as a reference gene. The real-time PCR master mix included 25 µL 2× universal master mix, 2.5 µL 20× detector set (with the primer and probe), and 21.5 µL of water. PCR was performed in an Applied Biosystems 7500 sequence detection system. The thermocycler conditions included denaturation at 95° C. for 15 seconds and annealing/extension at 60° C. for 60 seconds. Forty cycles of PCR were preceded by 95° C. for 10 minutes. Reactions were performed in triplicate. The relative quantities of genes were determined using the formula 2-AACt using the Applied Biosystems 7500 software.

Results

In vivo administration of purified potato polysaccharide preparation to ZDF rats (n=10) vs. vehicle control ZDF rats engendered a statistically significant enhancement of interactive LRP1, APBB1, IDE, and GPX3 gene expression, normalized as fold changes of 1.8, 1.9, 1.5, and 2.4, respectively, in adipose tissue samples, as depicted in Table 2. In similar fashion, in vivo administration of purified potato polysaccharide preparation to ZDF rats (n=7) vs. vehicle control ZDF rats engendered a statistically significant enhancement of interactive APBB1, IDE and GPX4 gene expression, normalized as fold changes of 1.7, 1.5, and 2.6, respectively, in blood samples, as depicted in Table 3. In vivo administration of purified potato polysaccharide preparation to ZDF rats (n=7) vs. vehicle control ZDF rats engendered a highly dramatic and statistically significant reduction of IGF1 and NOS2 proinflammatory gene expression, normalized as fold changes of −1.7 and −4.6, respectively, in blood samples, as depicted in Table 4.

TABLE 2

Enhanced gene expression of LRP1, APBB1, IDE, and GPX3 in adipose tissues of Zucker Diabetic Fatty vs. vehicle control ZDF rats (n = 10) following in vivo potato polysaccharide preparation administration.

| Gene Symbol | Fold Change | Description | p value |
|---|---|---|---|
| LRP1 | 1.8 | Low density lipoprotein receptor-related protein 1 | 0.02 |
| APBB1 | 1.9 | Amyloid beta precursor protein-binding, family B, member 1 | 0.0004 |
| IDE | 1.5 | Insulin degrading enzyme | 0.01 |
| GPX3 | 2.4 | Glutathione peroxidase 3 | 0.0004 |
| GPX4 | −1.1 | Glutathione peroxidase 4 | 0.6 |
| IGF1 | ND | Insulin like growth factor | — |
| NOS2 | ND | Nitric oxide synthase 2, inducible | — |

Data sets were derived by DNA microarray analyses, as described above.
ND = gene expression not detected.

TABLE 3

Enhanced gene expression of APBB1, IDE, and GPX4 in blood samples of Zucker Diabetic Fatty vs. vehicle control ZDF rats (n = 7) following in vivo potato polysaccharide preparation administration.

| Gene Symbol | Fold Change | Description | p value |
|---|---|---|---|
| APBB1 | 1.7 | Amyloid beta precursor protein-binding, family B, member 1 | 0.04 |
| IDE | 1.5 | Insulin degrading enzyme | 0.04 |
| GPX4 | 2.6 | Glutathione peroxidase 4 | 0.002 |
| GPX3 | ND | Glutathione peroxidase 3 | — |
| LRP1 | ND | Low density lipoprotein receptor-related protein 1 | — |

Data sets were derived by DNA microarray analyses, as described above.
ND = gene expression not detected.

TABLE 4

Reduced expression of IGF1, and NOS2 proinflammatory genes in blood samples of Zucker Diabetic Fatty vs. vehicle control ZDF rats (n = 7) following in vivo potato polysaccharide preparation administration.

| Gene Symbol | Fold Change | Description | p value |
|---|---|---|---|
| IGF1 | −1.7 | Insulin-like growth factor 1 | 0.02 |
| NOS2 | −4.8 | Nitric oxide synthase 2, inducible | 0.003 |

Data sets were derived by DNA microarray analyses, as described above.

Figure 35:
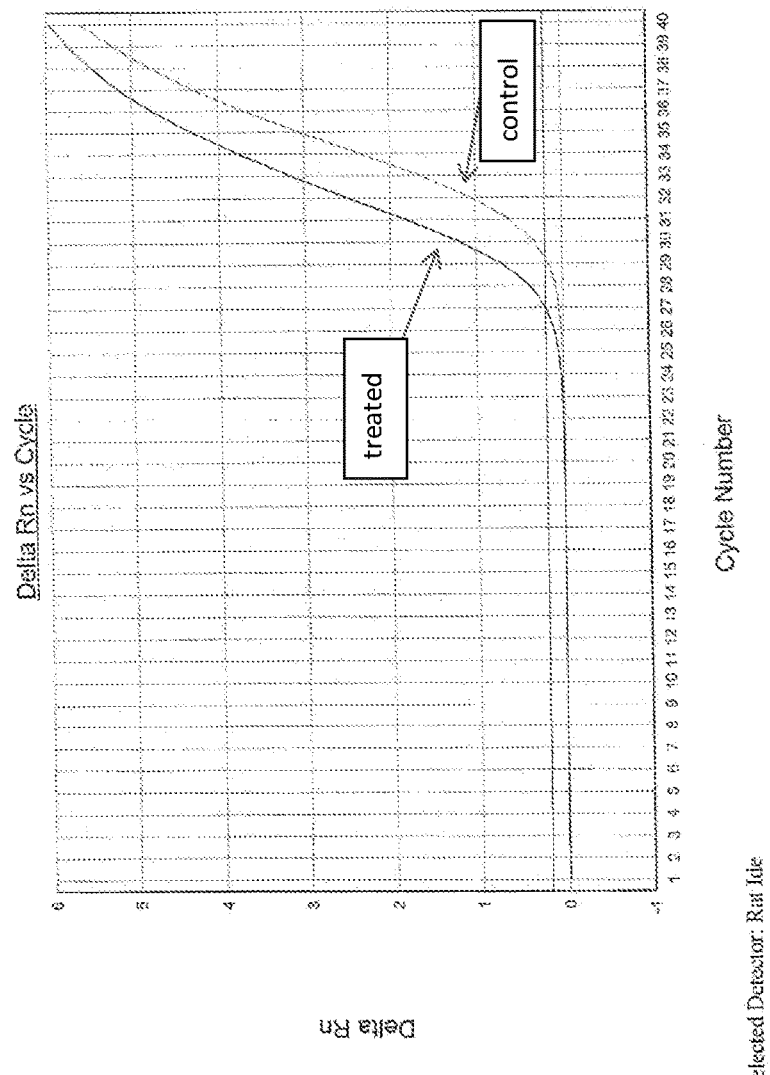
FIG. 35 is a real time PCR amplification plot for IDE demonstrating differences in threshold cycle numbers between potato polysaccharide preparation treated ZDF and untreated control ZDF in rat adipose tissue samples. The higher cycle number for the control rat's tissue equates to a lower gene expression.
Figure 36:
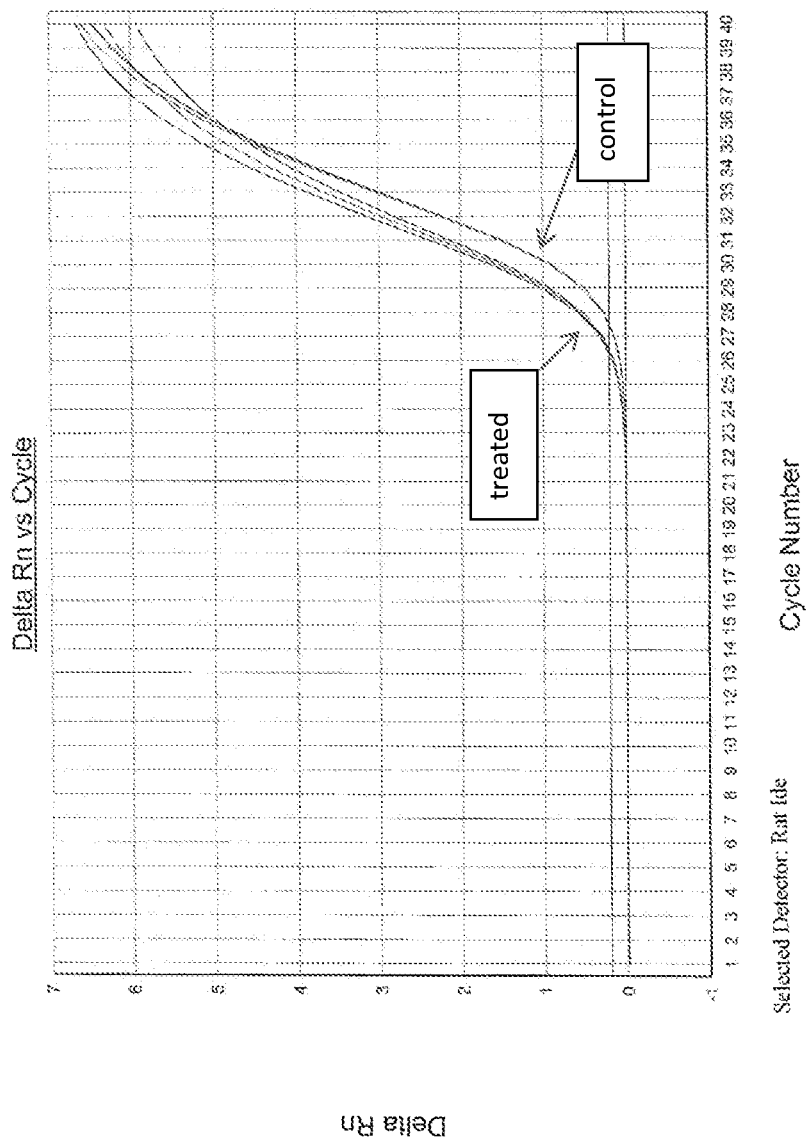
FIG. 36 is a Real time PCR amplification plot for IDE demonstrating differences in threshold cycle numbers between potato polysaccharide preparation treated ZDF and untreated control ZDF in rat blood samples. The higher cycle number for the control rat's tissue equates to a lower gene expression.
Figure 37:
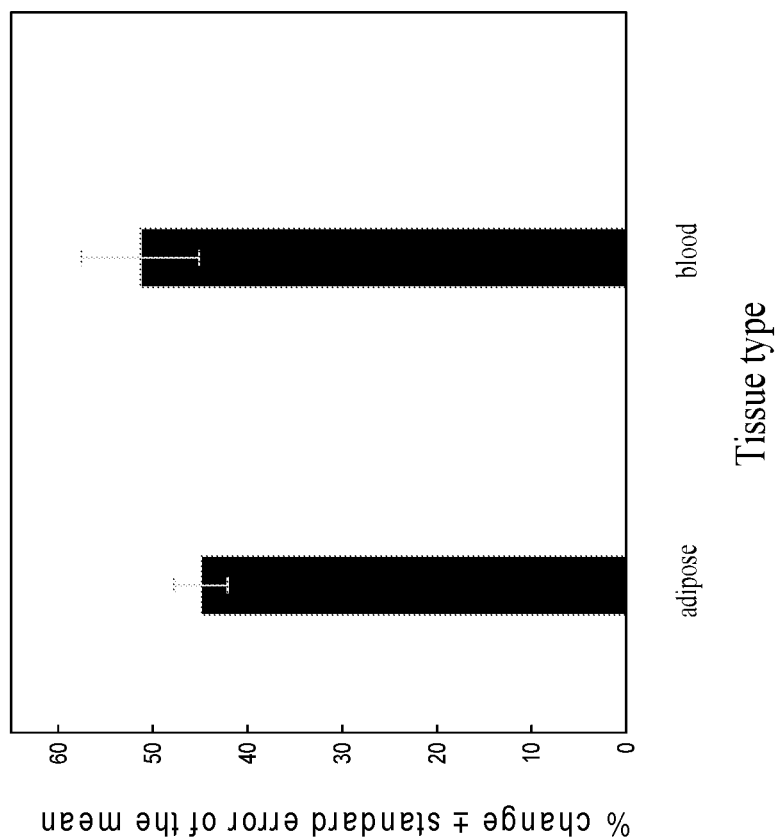
FIG. 37 is a graph plotting percent change in IDE gene expression, as measured by real time PCR analyses. The enhancements in IDE gene expression were determined to be 44.9±2.8% (n=9, p=0.02) and 51.3±6.2% (n=6, p=0.04), for adipose tissue and blood samples, respectively via Unpaired t-tests.

Real-time PCR analysis of IDE expression was performed to validate the DNA microarray data sets. In particular, the enhancement of IDE gene expression in adipose tissue and blood leukocyte samples, as monitored by DNA microarray analyses, was confirmed by real time PCR analyses. As depicted in FIG. 37, the enhancements in IDE gene expression were determined to be 44.9±2.8% (n=9, p=0.02) and 51.3±6.2% (n=6, p=0.04), for adipose tissue and blood samples, respectively. The respective real time PCR traces are depicted in FIGS. 35 and 36.

These results demonstrate that potato polysaccharide preparations can be used as anti-neurodegenerative agents to reduce amyloid beta levels within a mammal having Alzheimer's disease.

Example 5—Use of Potato Polysaccharide Preparations to Improve Cognition of APP SWE/PSEN1dE9 Mice Dosing and Grouping APP SWE/PSEN1dE9 mice are used as a model for Alzheimer's disease. The mice within the groups are chosen at random and divided into groups of X or Y. Groups are given dosages of potato polysaccharide preparation at a range of 0 mg/kg/day (control) up to 0.5 mg/kg/day. One dose is 0.15 mg/kg/day. The vehicle is distilled water, and the potato polysaccharide preparation is given daily each morning via oral gavage at the dosage to be evaluated. The dose is usually given in 1 mL of water. Mice are caged in groups and maintained in 12 hours light/12 hours dark (7 am-7 pm). The study proceeds for several months. A typical protocol starts with potato polysaccharide preparation administration at 20 weeks of age and continues through 30 weeks of age and includes 3 groups (20 animals/group): vehicle, 5 μg/day potato polysaccharide preparation, and 20 μg/day potato polysaccharide preparation.

Data Collection

Body weights are recorded weekly. Whole blood, serum, and plasma are collected at day 0 for baseline analysis. Whole blood, serum, and plasma are collected at termination. Brain tissue and vascular are collected and snap frozen in liquid nitrogen at termination. Whole genome microarrays are performed with the frozen tissue samples. Whole blood is preserved in PAX RNA blood tubes for possible gene expression analysis. Histology to determine the amount of plaque development in animal brain tissue is performed at termination. Any appropriate method to determine APP or AP4, amyloid beta polypeptides in blood or tissue is used. Cognition of the study animals is assessed by using the Morris water maze methodology.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing amyloid beta levels within a mammal having Alzheimer's disease, wherein said method comprises administering to said mammal a composition comprising a potato polysaccharide preparation obtained from raw potatoes, wherein said potato polysaccharide preparation, when derivatized, results in at least the following acylated carbohydrates as assessed using gas chromatography/mass spectography:
  (a) myo-inositol, set to 1x to serve as an internal standard,
  (b) glucose at about 40X to about 60X the myo-inositol content,
  (c) xylose at about 10X to about 20X the myo-inositol content, (d) mannose at about 5X to about 15X the myo-inositol content, and
(e) galactose at about 3X to about 7X the myo-inositol content, wherein the level of amyloid beta within said mammal is reduced.

2. The method of claim 1, wherein said mammal is a human.

3. The method of claim 1, wherein said level of amyloid beta within said mammal is reduced in blood.

4. The method of claim 1, wherein said level of amyloid beta within said mammal is reduced in adipose tissue.

5. The method of claim 1, wherein said composition comprises said potato polysaccharide preparation in an amount that results in between 0.05 mg and 50 mg of the potato polysaccharide component of said potato polysaccharide preparation being administered to said mammal per kg of body weight of said mammal.

6. The method of claim 1, wherein said composition comprises between 1 mg and 100 mg of said potato polysaccharide preparation.

7. The method of claim 1, wherein said composition comprises between 6 mg and 20 mg of said potato polysaccharide preparation.

8. The method of claim 1, wherein said composition comprises between 1 mg and 100 mg of the potato polysaccharide component of said potato polysaccharide preparation.

9. The method of claim 1, wherein said composition comprises between 6 mg and 20 mg of the potato polysaccharide component of said potato polysaccharide preparation.

10. The method of claim 1, wherein said composition is in the form of a tablet.

11. The method of claim 1, wherein said composition comprises alpha lipoic acid.

12. The method of claim 1, wherein said composition comprises alpha tocopherol.

13. The method of claim 1, wherein said potato polysaccharide preparation is in an amount that results in between 0.075 mg and 0.5 mg of the potato polysaccharide component of said potato polysaccharide preparation being administered to said mammal per kg of body weight of said mammal.

14. The method of claim 1, wherein at least about 80 percent of said potato polysaccharide preparation is potato polysaccharide.

15. The method of claim 1, wherein at least about 90 percent of said potato polysaccharide preparation is potato polysaccharide.

16. The method of claim 1, wherein at least about 95 percent of said potato polysaccharide preparation is potato polysaccharide.

* * * * *